(12) United States Patent
Kanai et al.

(10) Patent No.: US 7,744,537 B2
(45) Date of Patent: Jun. 29, 2010

(54) ULTRASONIC METHOD AND SYSTEM FOR CHARACTERIZING ARTERIAL TISSUE USING KNOWN ELASTICITY DATA

(75) Inventors: Hiroshi Kanai, Sendai (JP); Yoshiro Koiwa, Sendai (JP)

(73) Assignee: Japan Science and Technology Agency, Saitama (JP)

( * ) Notice: Subject to any disclaimer, the term of this patent is extended or adjusted under 35 U.S.C. 154(b) by 1357 days.

(21) Appl. No.: 10/487,517

(22) PCT Filed: Aug. 19, 2002

(86) PCT No.: PCT/JP02/08348

§ 371 (c)(1),
(2), (4) Date: Feb. 19, 2004

(87) PCT Pub. No.: WO03/015635

PCT Pub. Date: Feb. 27, 2003

(65) Prior Publication Data

US 2004/0260180 A1 Dec. 23, 2004

(30) Foreign Application Priority Data

Aug. 20, 2001 (JP) ............................. 2001-249398

(51) Int. Cl.
*A61B 8/00* (2006.01)
(52) U.S. Cl. .................................................. 600/453
(58) Field of Classification Search ................. 600/449, 600/443, 587
See application file for complete search history.

(56) References Cited

U.S. PATENT DOCUMENTS

| | | | | |
|---|---|---|---|---|
| 4,646,754 A * | 3/1987 | Seale | .................. | 600/587 |
| 4,771,792 A * | 9/1988 | Seale | .................. | 600/587 |
| 5,293,870 A | 3/1994 | Ophir et al. | | |
| 5,524,636 A * | 6/1996 | Sarvazyan et al. | .......... | 600/587 |
| 5,664,571 A * | 9/1997 | Yamazaki | .................. | 600/441 |
| 5,810,731 A * | 9/1998 | Sarvazyan et al. | .......... | 600/438 |
| 5,896,894 A * | 4/1999 | Schwamborn et al. | ...... | 138/110 |
| 6,278,890 B1 * | 8/2001 | Chassaing et al. | ........... | 600/407 |
| 6,748,259 B1 * | 6/2004 | Benaron et al. | ............. | 600/476 |

(Continued)

FOREIGN PATENT DOCUMENTS

JP 5-501825 4/1993

(Continued)

OTHER PUBLICATIONS

WO/1999/47046.*

(Continued)

*Primary Examiner*—Brian Casler
*Assistant Examiner*—Parikha S Mehta
(74) *Attorney, Agent, or Firm*—McGlew and Tuttle, P.C.

(57) ABSTRACT

In a method for identifying a living tissue in an ultrasonic diagnosis, the elasticity of a living tissue to be diagnosed is measured for each local small area by using ultrasound. Elasticity data for each kind of known living tissue is composed of an elasticity modulus frequency histogram in each local small area for each kind of living tissue and is managed in a data library. Regarding the elasticity data serving as the measurement results, the kind of living tissue to be diagnosed is identified by using the elastic data for each kind of known living tissue.

9 Claims, 17 Drawing Sheets

U.S. PATENT DOCUMENTS

| | | | |
|---|---|---|---|
| 6,979,293 B2 * | 12/2005 | Hansmann et al. | 600/439 |
| 7,113,817 B1 * | 9/2006 | Winchester et al. | 600/476 |
| 2001/0039381 A1 * | 11/2001 | Burns et al. | 600/443 |
| 2002/0010406 A1 * | 1/2002 | Douglas et al. | 600/583 |

FOREIGN PATENT DOCUMENTS

| | | | |
|---|---|---|---|
| JP | 10-5226 | | 1/1998 |
| JP | 2000-229078 | | 8/2000 |
| JP | 2002-506666 | | 3/2002 |
| WO | WO 91/17517 | | 11/1991 |
| WO | WO 99/47046 | | 9/1999 |
| WO | WO 00/04831 | * | 2/2000 |

OTHER PUBLICATIONS

H. Kanai et al., 1997, Noninvasive evaluation of local myocardial thickening and its color-coded Imaging, *IEEE Transaction UFFC*. 1997; 44:752-768.

H. Hasegawa et al., 1998, Accuracy evaluation in the measurement of a small change in the thickness of arterial walls and the measurement of elasticity of the human carotid artery, *Jpn J Appl. Phys 1998*; 37:3101-3105.

H. Kanai et al., 1999, Real-time measurements of local myocardium motion and arterial wall thickening, *IEEE Transaction UFFC*. 1999; 46:1229-1241.

H. Kanai et a., 2001, Ultrasonic-based tissue characterization system of arterial wall for treatment, *Journal of Medical Ultrasonics*, Apr. 15, 2001, vol. 28, No. 3, p. J286.

A. Umezawa et al., Aug. 1998, Measurement of local pulse wave velocity for evaluation of viscoelasticity from small vibrations on artery measured using ultrasound, *The Institute of Electronics, Information and Communication Engineers Gijutsu Kenkyu Hokoku*, vol. 99, No. 26, pp. 17 to 23.

S. Levinson et al., 1995, Sonoelastic determination of human skeletal muscle elasticity, *Journal of Biomechanics*, vol. 28, No. 10, pp. 1145 to 1154.

Y. Yamakoshi, 2001, Ultrasonic imaging of elastic properties of soft tissue from shear wave propagation measurement, *Journal of Medical Ultrasonics*, Apr. 15, 2001, vol. 28, No. 3, p. J293.

* cited by examiner

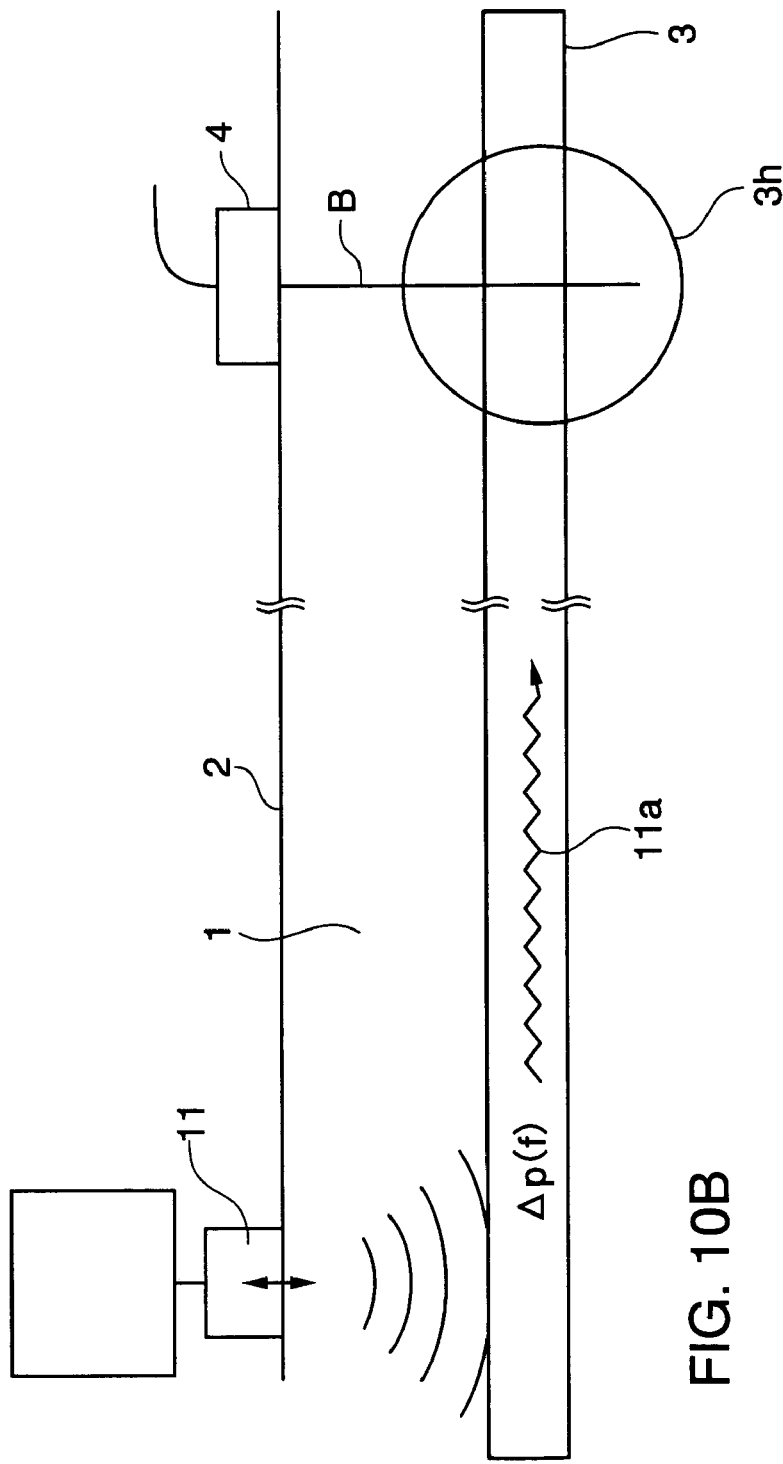
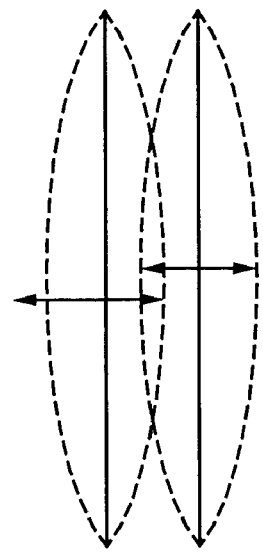

ULTRASONIC METHOD AND SYSTEM FOR CHARACTERIZING ARTERIAL TISSUE USING KNOWN ELASTICITY DATA

TECHNICAL FIELD

This invention relates to a method for identifying a living tissue in an ultrasonic diagnosis and an ultrasonic diagnosis system, and more particularly to a method for identifying a living tissue in an ultrasonic diagnosis, in which ultrasound is used to carry out a diagnosis of a lesion on a living tissue according to a noninvasive measurement, and an ultrasonic diagnosis system, thereby the kind of tissue such as a lipid-rich (or fatty) area, a thrombus area, an elastic fiber, a collagen fiber, and a calcified area is identified and is displayed in an effective manner for a diagnosis of a local lesion such as an atheroma in a blood vessel.

BACKGROUND ART

Until now myocardial infarction, angina pectoris, cerebral infarction, and so on have been considered to be the development of a stenosis on a blood vessel which perfuses organs. However, it has become evident that these diseases are caused by the susceptibility of an atheroma to rupture. The atheroma is a blood wall disease. Actually according to a clinical examination of a cholesterol-lowering agent used worldwide, the remarkable effect of improving a survival rate and preventing myocardial infarction is obtained even through the stenosis of a blood vessel hardly changes. This is because the agent stabilizes an atheroma as a tissue. In consideration of this fact, a method for examining the susceptibility of an atheroma to rupture (susceptibility to rupture) has been demanded. A conventional method such as X-ray CT, MRI, and angiography cannot carry out such an examination.

For example, in view of an accurate measurement on a blood vessel disease, conventional echocardiography M-mode just has a resolution of 1 mm. Similarly when the vibration of an aorta is determined as a displacement velocity by conventional Doppler method, conditions for accuracy are theoretically satisfied but the pulsation of a blood vessel greatly affects in reality. Thus, it is difficult to extract a small vibration superimposed to a relatively large amplitude. Hence, researchers including the inventor have developed a phased tracking method whereby a small vibration on a beating heart and a large blood vessel is remotely measured by ultrasound and an elasticity modulus of a blood vessel wall can be calculated on a given spot. Thus, it is possible to accurately diagnose the susceptibility of an atheroma to rupture (Reference Documents 1 to 5).

The following are reference documents:
1. Kanai H, Hasegawa H, Chubachi N, Koiwa Y, Tanaka M. Noninvasive evaluation of local myocardial thickening and its color-coded Imaging. IEEE transaction UFFC. 1997; 44: 752-768;
2. Hasegawa H, Kanai H, Hoshimiya N, Chubachi N, Koiwa Y. Accuracy evaluation in the measurement of a small change in the thickness of arterial walls and the measurement of elasticity of the human carotid artery. Jpn J Appl Phys 1998; 37: 3101-3105;
3. Kanai H, Koiwa Y, J. Zhang Real-time measurements of local myocardium motion and arterial wall thickening. IEEE-transaction UFFC. 1999; 46: 1229-1241;
4. Japanese Patent Laid-Open No. 10-5226; and
5. Japanese Patent Laid-Open No. 12-229078.

The phased tracking method will be schematically described below. The phased tracking method is a new bio-instrumentation for measuring a small vibration velocity on a cardiac wall and a blood vessel wall. This method makes it possible to accurately measure a vibration of 500 Hz or less and 0.01 mm and a change of 10 microns on a wall. With this method, for example, small velocities on a plurality of measurement points between the layer (or layers) in the arterial wall or on the wall of an arterial vessel are determined by ultrasonic Doppler method, and the small velocities on the measurement points are subjected to time quadrature, so that a time change in the positions of the measurement points can be calculated. Since a change in layer thickness can be determined by the time change in the positions of the measurement points, the elasticity modulus of the layer can be obtained, thereby estimating susceptibility to rupture.

Actually as shown in FIG. 17, an arterial intramural measurement point on an ultrasonic beam 91 is set at (i) and a measurement point with the subsequent depth is set at (i+1). Small vibration velocities $v_i(t)$ and $v_{i+1}(t)$ on the measurement points are determined and a difference between the small vibration velocities is subjected to time quadrature, so that a change $\Delta h(t)$ in layer thickness between the measurement points (i) and (i+1) in the arterial wall is determined. Reference numeral 92 denotes a plaque.

$$\Delta h(t) = \int_{-\infty}^{t} \{v_i(t) - v_{i+1}(t)\} dt$$

The simplest method for converting the change into an elasticity value for each layer in the arterial wall is performed as follows: a wall thickness is set at hd and a change in thickness is set at Δh at the lowest blood pressure where a wall thickness increases, a pulse pressure at a cuff pressure on brachial artery is set at ΔP, and a wall elasticity modulus is measured for each layer in the following manner.

Based on a thickness change (Δh) of each layer from the intima to the adventitia of a blood vessel, an elasticity value (En) of each small part (n) in a blood vessel wall atheroma is determined by the formula below.

$$En=(\Delta P/(\Delta h/hd)n)$$

With this phased tracking method, it is possible to measure an elasticity value for each layer along the depth direction in a blood vessel wall approximately every 0.75 mm to 0.075 mm on an ultrasonic beam, thereby displaying a tomogram based on the elasticity values.

In a clinical diagnosis using the phased tracking method, when an elasticity value is examined for each layer of a blood vessel wall, the elasticity value ranges from 100 to 2 MPa in a normal person. However, in the example of an atheroma, elasticity values are not evenly distributed. It is understood that fundamentally a physically soft portion is present in a thrombus and is covered with a hard portion. In addition, various patterns are present in the tomogram of an atheroma. For example, an extremely soft substance is exposed on the lumen of a blood vessel without continuity on a capsule of a hard surface, and a substance having a large elasticity value almost entirely covers a surface. Elasticity values in an atheroma are distributed from 0 to 4 MPa. Further, according to the examination results on the correspondence of a lipid-rich layer and a collage fiber in an extracted blood vessel and elasticity values in the phased tracking method, there is a probability that the tissue image of a collagen fiber covering an atheroma can be separately displayed from a tomogram of elasticity values, the tomogram being obtained in a noninvasive manner.

It is an object of the present invention to provide more specific information displayed in a tomogram and to identify the kind of living tissue such as a lipid-rich area, a thrombus area, an elastic fiber, a collagen fiber, and a calcified area in an ultrasonic diagnosis of a living tissue such as a lesion on a blood vessel.

It is another object of the present invention to identify the kind of living tissue such as a lipid-rich area, a thrombus area, an elastic fiber, a collagen fiber, and a calcified area by using a shear elasticity modulus and a shear viscosity in an ultrasonic diagnosis of a living tissue such as a lesion on a blood vessel.

DISCLOSURE OF INVENTION

A method for identifying a living tissue in an ultrasonic diagnosis and an ultrasonic diagnosis system according to the present invention are realized in the following structures.

The method for identifying a living tissue in an ultrasonic diagnosis according to the present invention includes measuring at least the elasticity of a living tissue to be diagnosed in each local small area by using ultrasound; managing, in a data library, at least elasticity data for each kind of known living tissue, the elasticity data being composed of an elasticity modulus frequency histogram in each local small area for each kind of living tissue; and identifying the kind of living tissue to be diagnosed, at least regarding the elasticity data serving as measurement results, by using the elasticity data for each kind of known living tissue.

Further, the method for identifying a living tissue in an ultrasonic diagnosis preferably includes exciting a vibration on a measured part of the living tissue to be diagnosed; measuring a shear elasticity and a shear viscosity of the excited living tissue to be diagnosed in the measurement using ultrasound; managing viscosity data for each kind of known living tissue in the management of the data library, the viscosity data being composed of a viscosity frequency histogram in each local small area for each kind of living tissue; and identifying the kind of living tissue to be diagnosed, regarding the elasticity data and viscosity data serving as measurement results, by using the elasticity data and viscosity data for each kind of known living tissue in the identification of the kind of living tissue to be diagnosed.

Further, the method for identifying a living tissue in an ultrasonic diagnosis according to the present invention, wherein the vibration on the measured part of the living tissue to be diagnosed is preferably excited by a turbulent flow component or a vortex component, the components being generated by a time change in a pulse of a pulsatile flow in a blood vessel.

Moreover, the method for identifying a living tissue in an ultrasonic diagnosis according to the present invention, wherein the vibration on the measured part of the living tissue to be diagnosed is preferably excited by a vibration percutaneously applied to a part away from the measured part from the outside of a body.

Additionally, the method for identifying a living tissue in an ultrasonic diagnosis according to the present invention, wherein in the management of the data library, each kind of known living tissue is preferably mapped on a two-dimensional plane having axes representing a shear elasticity modulus and a shear viscosity.

Besides, the method for identifying a living tissue in an ultrasonic diagnosis according to the present invention, wherein the living tissue to be diagnosed is preferably a living tissue on a heart, a blood vessel, and so on.

Further, the method for identifying a living tissue in an ultrasonic diagnosis according to the present invention, wherein the kind of known living tissue preferably includes a lipid-rich area, a thrombus area, an elastic fiber, a collagen fiber, and a calcified fiber.

Moreover, the method for identifying a living tissue in an ultrasonic diagnosis according to the present invention, wherein the local small area serving as a unit to measure the elasticity of the living tissue to be diagnosed is preferably several tens to several hundreds square microns.

Besides, the method for identifying a living tissue in an ultrasonic diagnosis according to the present invention, wherein the kind of living tissue to be diagnosed is identified using the elasticity data serving as measurement results, and the identification is preferably performed by referring to the elasticity data for each kind of known living tissue, the data being extracted from the data library, and determining the kind of known living tissue having the minimum distance.

Moreover, the method for identifying a living tissue in an ultrasonic diagnosis according to the present invention, wherein the kind of known living tissue having the minimum distance from the elasticity data serving as measurement results is preferably determined by using Bayes decision method for dispersion and an average value of the elasticity moduli determined from the histogram of elasticity data on each kind of known living tissue.

Additionally, the method for identifying a living tissue in an ultrasonic diagnosis according to the present invention, wherein an electronic chromatic figure is preferably generated and displayed so as to identify in colors the kind of living tissue to be diagnosed, the kind of living tissue being identified for each local small area.

An ultrasonic diagnostic system of the present invention, in which at least the elasticity of a living tissue to be diagnosed is measured for each local small area by using ultrasound and a tomogram is displayed, the system includes a data library for managing at least elasticity data in each kind of known living tissue, the elasticity data being composed of an elasticity modulus frequency histogram in each local small area for each kind of living tissue, and a tissue identifying unit to identify the kind of living tissue to be diagnosed, regarding at least the elasticity data serving as measurement results, by using the elasticity data for each kind of know living tissue.

Further, the ultrasonic diagnostic system preferably includes exciting means for exciting a vibration on a measured part of a living tissue to be diagnosed, wherein the data library further includes viscosity data for each kind of known living tissue and manages the viscosity data for each kind of known living tissue, the viscosity data being composed of a viscosity frequency histogram in each local small area for each kind of living tissue, and the tissue identifying unit identifies the kind of living tissue to be diagnosed, regarding the elasticity data and viscosity data serving as measurement results of the excited living tissue to be diagnosed, by using the elasticity data and viscosity data for each kind of known living tissue.

Moreover, the ultrasonic diagnostic system of the present invention, wherein each kind of known living tissue is preferably mapped on a two-dimensional plane having axes representing a shear elasticity modulus and a shear viscosity.

Besides, the ultrasonic diagnostic system of the present invention, wherein the living tissue to be diagnosed is preferably a living tissue on a heart, a blood vessel, and so on.

Additionally, the ultrasonic diagnostic system of the present invention, wherein the kind of known living tissue preferably includes a lipid-rich area, a thrombus area, an elastic fiber, a collagen fiber, and a calcified fiber.

Further, the ultrasonic diagnostic system of the present invention, wherein the local small area serving as a unit to measure the elasticity of the living tissue to be diagnosed is preferably several tens to several hundreds square microns.

Moreover, the ultrasonic diagnostic system of the present invention, wherein the tissue identifying unit preferably has identifying means which refers to the elasticity data for each kind of known living tissue, the data being extracted from the data library, and determines the kind of known living tissue having the minimum distance, for each elasticity data serving as measurement results in each local small area.

Besides, the ultrasonic diagnostic system of the present invention, wherein the identifying means preferably determines dispersion and an average value of the elasticity moduli from the histogram of elasticity data of each kind of known living tissue, the data being extracted from the data library, and the identifying means performs identification using Bayes decision method.

Additionally, the ultrasonic diagnostic system of the present invention, wherein the tissue identifying unit has electronic chromatic figure generating means for generating an electronic chromatic figure so as to identify in colors the kind of living tissue to be diagnosed, the kind of living tissue being identified for each local small area.

BRIEF DESCRIPTION OF DRAWINGS

FIG. 2 is an explanatory drawing showing the generation of an elasticity modulus tomogram, and especially

FIG. 10 is a conceptual drawing showing a vibration excited on a blood vessel wall.

FIG. 13 is a diagram showing a tomogram, and especially

FIG. 14 is a diagram showing a tomogram, and especially

BEST MODE FOR CARRYING OUT THE INVENTION

Embodiment 1

In this example, the conventional problem is solved as follows: based on findings that tissues such as a lipid-rich area, a thrombus area, an elastic fiber, a collagen fiber, and a calcified area that are found on a blood vessel wall are different in hardness according to tissue characteristics, the frequency distribution (histogram) concerning an elasticity value for each kind of tissue is acquired beforehand and is managed in a data library, each local elasticity value obtained in an ultrasonic diagnosis is compared with the frequency distribution of the elasticity values of the tissues in the data library, a tissue is discriminated by determining the tissue having a frequency distribution of the closest elasticity value, and tissue type information is displayed, for example, in colors in a tomogram.

Figure 1:
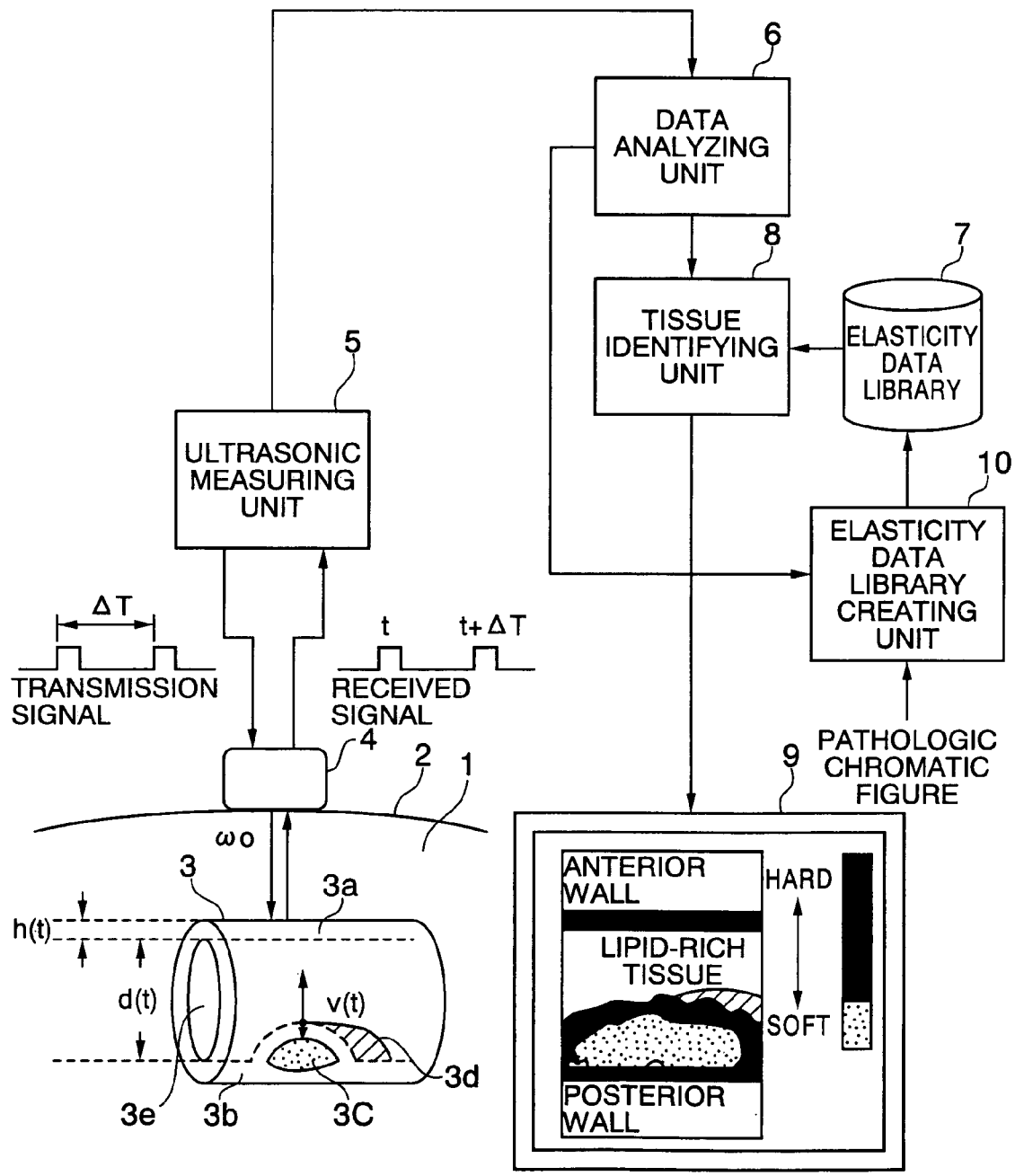
FIG. 1 is a schematic structural diagram showing an ultrasonic diagnostic system according to the present invention.

FIG. 1 is a schematic structural diagram showing an ultrasonic diagnostic system according to the present invention.

In FIG. 1, reference numeral 1 denotes a human body, reference numeral 2 denotes the surface of the body, and reference numeral 3 denotes a blood vessel including an artery to be measured. In the blood vessel, a blood vessel wall has a thickness of h(t), a lumen has a diameter of d(t), and a vibration is made at a movement velocity of v(t). Reference numeral 3a denotes the anterior wall of the blood vessel. Reference numeral 3b denotes the posterior wall of the blood vessel. Reference numeral 3c denotes a lesion such as an atheroma appearing in the blood vessel 3. Reference numeral 3d denotes a lipid-rich tissue. Reference numeral 3e denotes the lumen of the blood vessel 3. Reference numeral 4 denotes an ultrasonic probe which can change the emitting direction of an ultrasonic beam to perform scanning over a certain range. Reference numeral 5 denotes an ultrasonic measuring unit which generates a transmission signal with an angular frequency of $\omega_0$ at a fixed time interval $\Delta T$ to drive the ultrasonic probe 4 and radiates an ultrasonic beam to the blood vessel 3. When the ultrasonic probe 4 receives a reflected wave from the blood vessel 3, the received signal of the probe is subjected to quadrature demodulation and AD conversion and a detection signal is outputted in a digital signal format.

Reference numeral 6 denotes a data analyzing unit. The data analyzing unit 6 analyzes the detection signal, which has been outputted in a digital signal format from the ultrasonic measuring unit 5, according to phased tracking method, performs tracking on the track of the large amplitude displacement of the blood vessel 3, and determines a small vibration velocity of each reflection point on the surface of the blood vessel wall and between layers on the track. According to the result, a time change is calculated for the thickness of the blood vessel wall or each of the layers. An elasticity modulus of a tissue on the blood vessel wall or each of the layers is accurately calculated based on the time change in each small area determined by a resolving power, and elasticity modulus tomogram data is generated. In this tracking, the displacing motion of a small vibration in the layers of the blood vessel is analyzed under the constraint that a cumulative displacement in a pulse is set at 0 so as to make a return to the original position at each pulse of the heart, thereby stabilizing an image.

Reference numeral 7 denotes an elasticity data library used as the reference (a kind of dictionary) of tissue identification.

The elasticity data library 7 stores elasticity data concerning kinds of living tissues. The data has been inputted beforehand and serves as the reference. To be specific, the elasticity data library 7 stores frequency distribution (histogram) data concerning an elasticity value of each kind of known living tissue. Further, an average value and dispersion may be calculated from the frequency distribution data and may be replaced with the frequency distribution.

Reference numeral 8 denotes a tissue identifying unit, in which regarding an elasticity value on each point of the elasticity modulus tomogram data generated by the data analyzing unit 6, the elasticity data concerning various kinds of living tissues is extracted from the elasticity data library 7, the elasticity data serving as the reference, a comparison is made, the closest kind of living tissue is discriminated, and electronic chromatic figure data is generated. In the electronic chromatic figure data, the area of the elasticity modulus tomogram is displayed in colors corresponding to the kinds of tissues.

Reference numeral 9 denotes a display device which displays an electronic chromatic figure based on the electronic chromatic figure data generated by the tissue identifying unit 8.

Reference numeral 10 denotes an elasticity data library creating unit, in which regarding data effectively acting as the reference in the elasticity modulus tomogram data generated by the data analyzing unit 6, a comparison is made with a pathologic chromatic figure generated in advance, so that the kind of living tissue is identified in each local area of the tomogram, and attribute data indicating the kind of living tissue is inputted and set in the elasticity modulus tomogram data. Then, attribute data in each local area is examined, and the frequency distribution of an elasticity modulus is determined for each kind of living tissue and is registered in the elasticity data library 7.

The embodiment of the ultrasonic diagnostic system shown in FIG. 1 will be discussed in detail below.

Figure 2A:
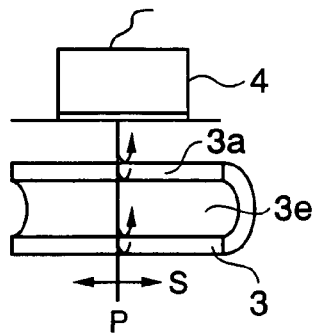
FIG. 2A shows one scanning position of an ultrasonic beam.
Figure 2B:
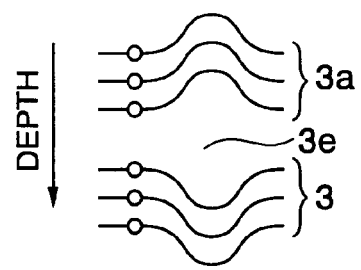
FIG. 2B shows the calculation of displacement waveforms.
Figure 2C:
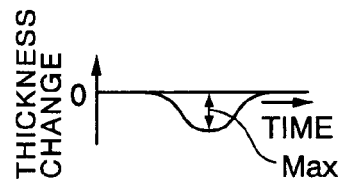
FIG. 2C shows a thickness change waveform.
Figure 2D:
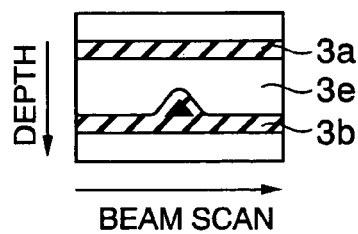
FIG. 2D shows an elasticity modulus tomogram.
Figure 2E:
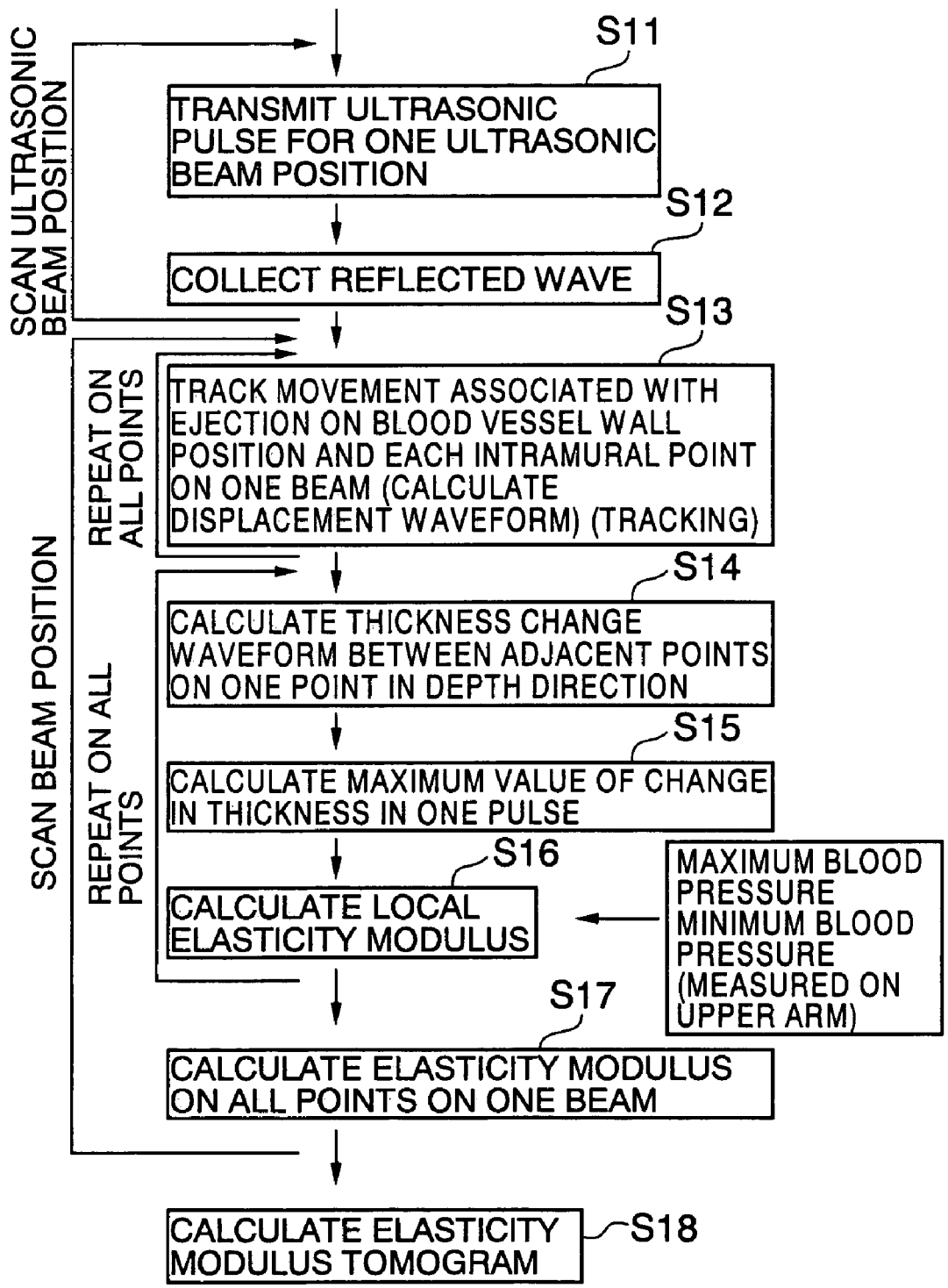
FIG. 2E shows the overall flow of the generation of an elasticity modulus tomogram.

FIG. 2E shows the overall flow of the generation of an elasticity modulus tomogram that corresponds to conventional processing performed by the ultrasonic measuring unit 5 and the data analyzing unit 6 of FIG. 1. As shown in FIG. 2A, a blood vessel area to be diagnosed on a living tissue is scanned by the ultrasonic probe along an arrow S, an ultrasonic pulse is transmitted at each scanning position (beam position P) at a regular interval (step S11), and reflected waves are collected from the anterior wall and posterior wall of a blood vessel and boundaries between the layers of the blood vessel (step S12). Step S11 and step S12 are repeated by the ultrasonic measuring unit 5 at each scanning position of an ultrasonic beam position.

Subsequently, data of the reflected waves collected by the data analyzing unit 6 is analyzed. First, as shown in FIG. 2B, regarding points (indicated by circles) on the surface of the blood vessel wall and boundaries between the layers of the blood vessel on one beam, displacement waveforms are calculated and tracking is performed to track the large amplitude motion generated on the blood vessel by heart stroke (step S13). Step S13 is repeated on all the points of one beam. Then, between adjacent points of FIG. 2A, a thickness change waveform is calculated as shown in FIG. 2C (step S14). In this example, at the largest diameter of the lumen in FIG. 2B, a thickness change in FIG. 2C has the maximum value Max, which indicates the smallest thickness. The maximum value of the thickness change in a pulse is calculated (step S15). By using the value and a difference between the maximum blood pressure and the minimum blood pressure of a cuff pressure measured on an upper arm, a local elasticity modulus is calculated (step S16). Steps S14 to S16 are repeated on all the points. When local elasticity moduli are calculated for layers between all the adjacent points on one beam scanning position (step S17), a shift is made to the subsequent beam scanning position, steps S13 to S17 are repeated, and local elasticity moduli are similarly calculated for layers between all the adjacent points. In this way, local elasticity moduli are calculated on all the beam scanning positions and an elasticity modulus tomogram is calculated, in which the local elasticity modulus of a diagnostic area is indicated by a pixel value or a color attribute as shown in FIG. 2D (step S18).

Figure 3:
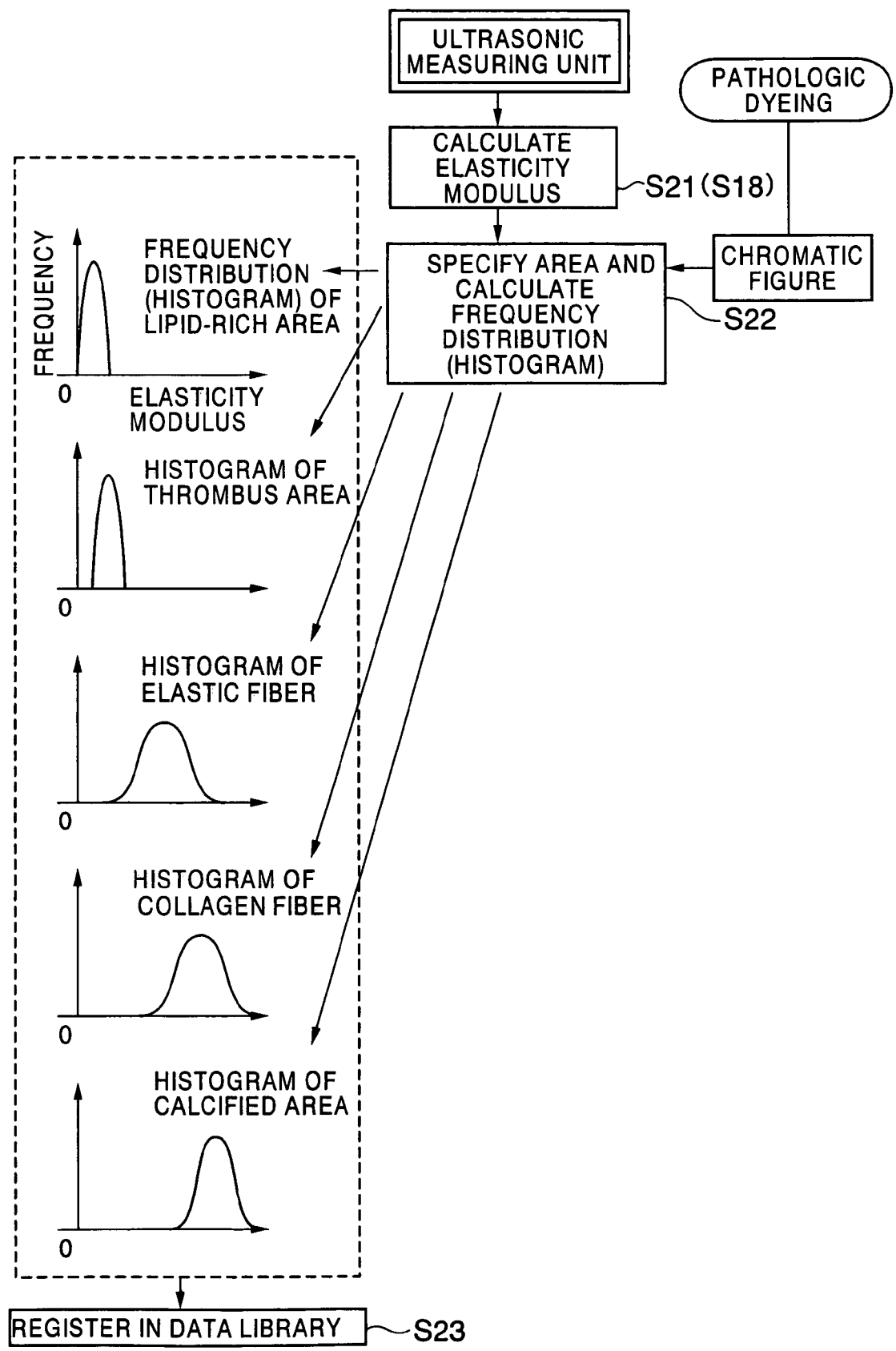
FIG. 3 is a schematic diagram showing the creation of an elasticity data library.

FIG. 3 is a schematic diagram showing the generation of the elasticity data library that corresponds to the processing of the elasticity data library creating unit 10 shown in FIG. 1. In the generation of the elasticity data library, regarding a suitable living tissue to be used as the reference of tissue identification, an area of an elasticity modulus tomogram is classified for each kind of tissue, and the frequency distribution (histogram) of an elasticity modulus is calculated for each kind of tissue and is registered in the elasticity data library. Hence, an ultrasonic measurement part, that is the elasticity modulus tomogram calculated by the flow of FIG. 2 is displayed on a screen (step S21) and another sample tissue is compared with an actual chromatic figure, in which a specific kind of tissue is dyed by pathologic dyeing, so that each kind of tissue area is identified in the elasticity modulus tomogram and area specification is performed on each kind of tissue (step S22). The example of FIG. 3 has five kinds of tissues including a lipid-rich area, a thrombus area, an elastic fiber, a collagen fiber, and a calcified area. In this way, after the setting of an area for each kind of tissue required for the elasticity modulus tomogram, the frequency distribution of an elasticity modulus is calculated for each resolution area such as a pixel in each area for each kind of tissue (step S22) and the results are registered in the elasticity data library (step S23).

Figure 4:
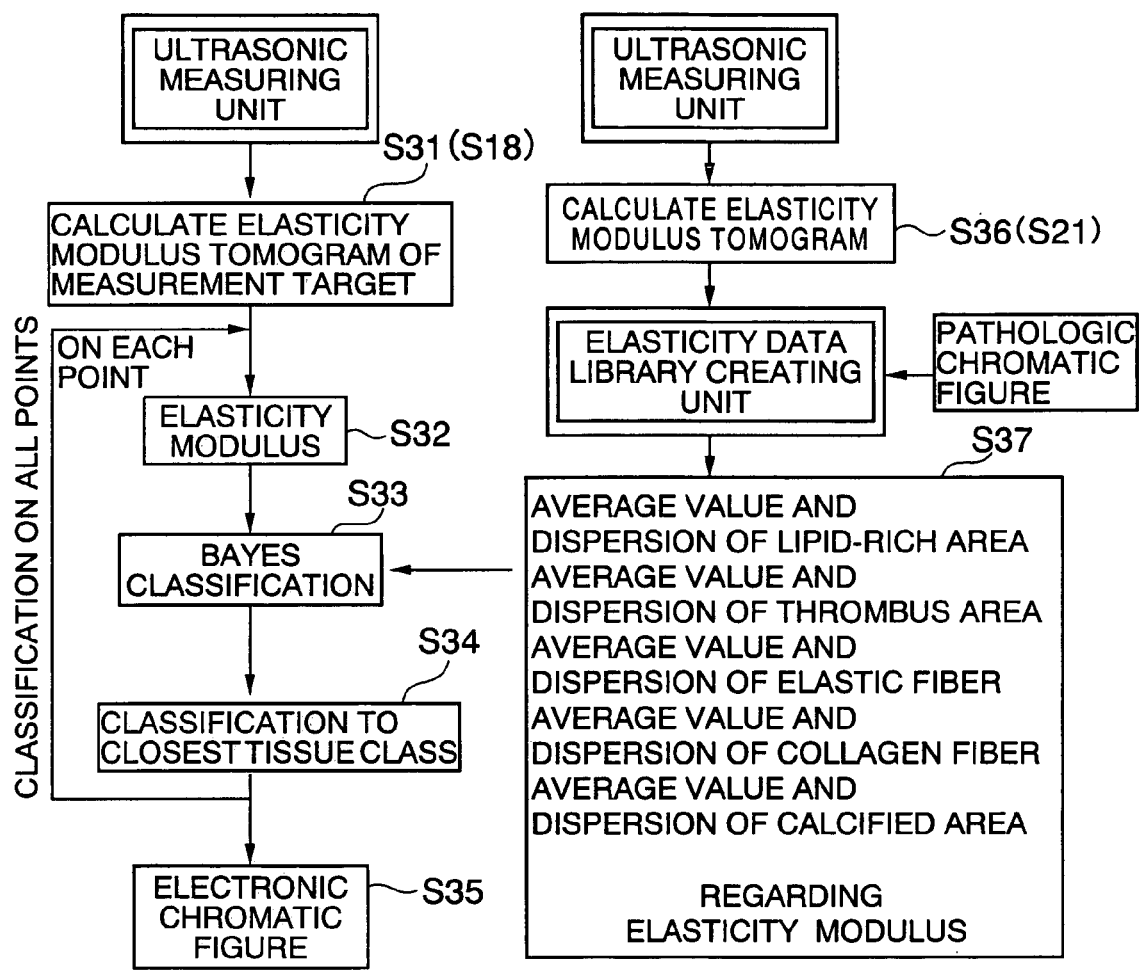
FIG. 4 is a flow showing tissue identification.

FIG. 4 shows the flow of tissue identification that corresponds to the processing of the tissue identifying unit 8 shown in FIG. 1. In tissue identification, the following processing is repeated: on each point of the elasticity modulus tomogram of a measured living body, the elasticity modulus is classified to the closest kind of tissue with reference to elasticity modulus frequency distribution data of tissues registered in the elasticity data library. In this example, Bayes decision method (Bayes classification method) is used as a mathematical method for tissue identification. Bayes decision method is one of statistical estimation methods. In this method, regarding the frequency distribution of a kind of tissue that is most likely to have an elasticity modulus on one point of the elasticity modulus tomogram, an estimation is made so that a defined loss function has the minimum expected value. This estimation corresponds to the selection of a similar pattern of the minimum distance in pattern recognition.

First, the elasticity modulus tomogram of a measured living body is determined by the processing of FIG. 2 (step S31). On the other hand, from the elasticity data library generated based on the calculation of the elasticity modulus tomogram (step S36) in the processing of FIG. 3, elasticity modulus frequency distribution data is read regarding five kinds including a lipid-rich area, which serves as a candidate of tissue classification, and an average value and dispersion are calculated for each elasticity modulus distribution (Step S37). Then, elasticity moduli on the points of the elasticity modulus tomogram are sequentially extracted (step S32), Bayes decision is performed by using values determined in step S37 (step S33), and the elasticity modulus is classified as a minimum-distance tissue in processing results (step S34). Steps S32 to S34 are repeated on all the points of the elasticity modulus tomogram. In this way, an elasticity modulus on each point of the elasticity modulus tomogram is classified as a proper tissue and an electronic chromatic figure is generated (step S35).

Figure 5:
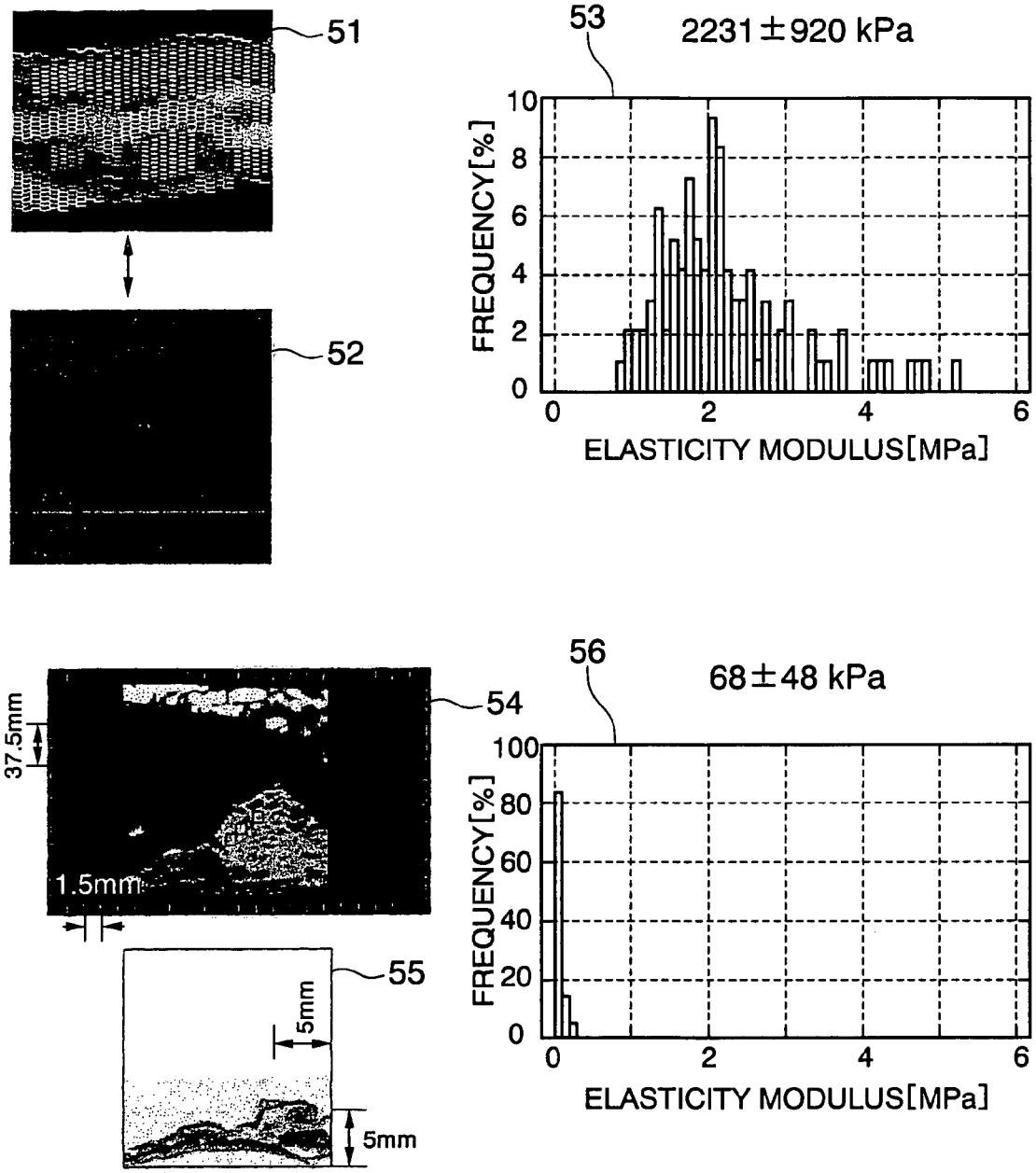
FIG. 5 is a diagram showing the measurement results of elasticity moduli of a fiber tissue.
Figure 6:
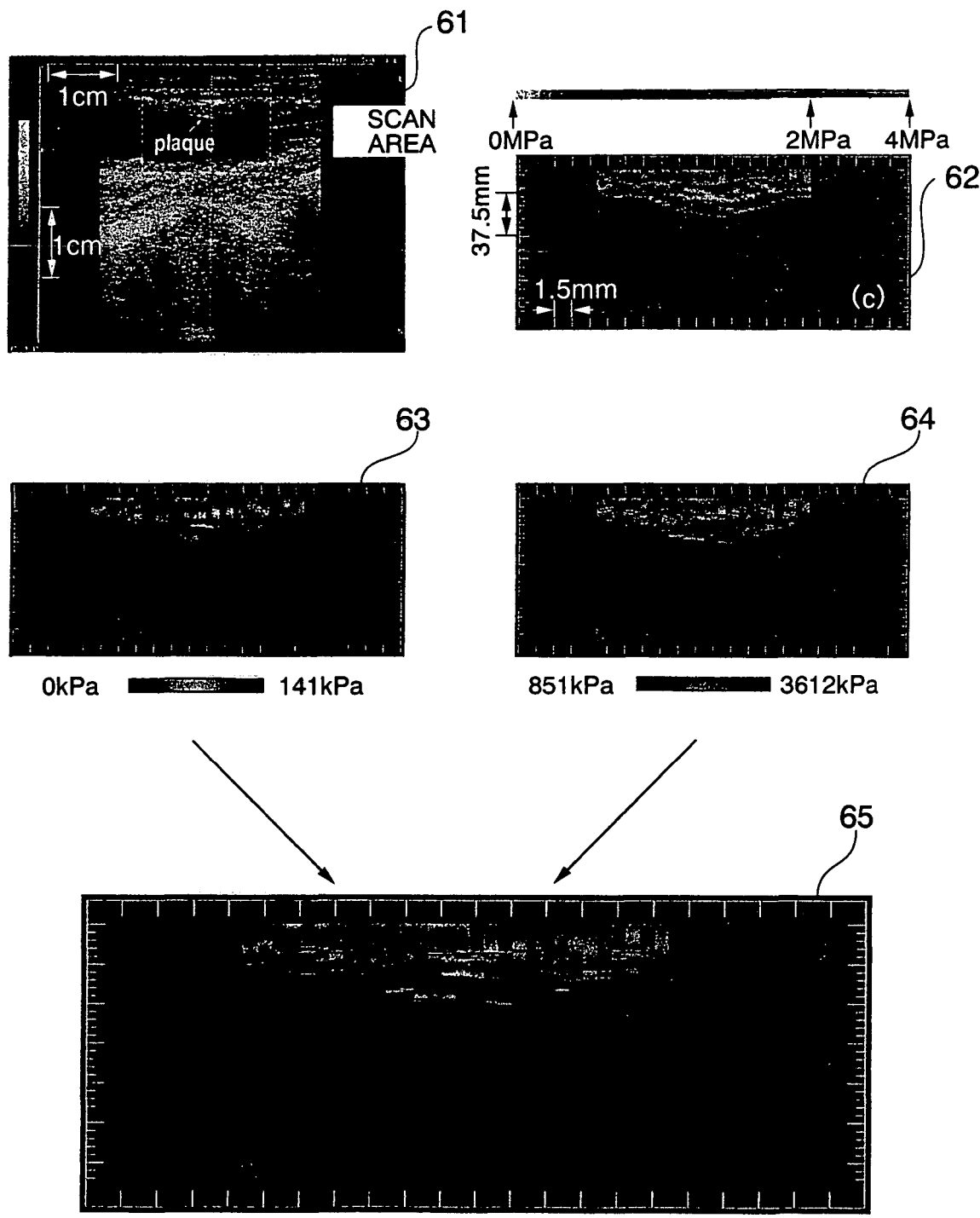
FIG. 6 is a diagram showing an example of tissue identification (71-year-old man).
Figure 7:
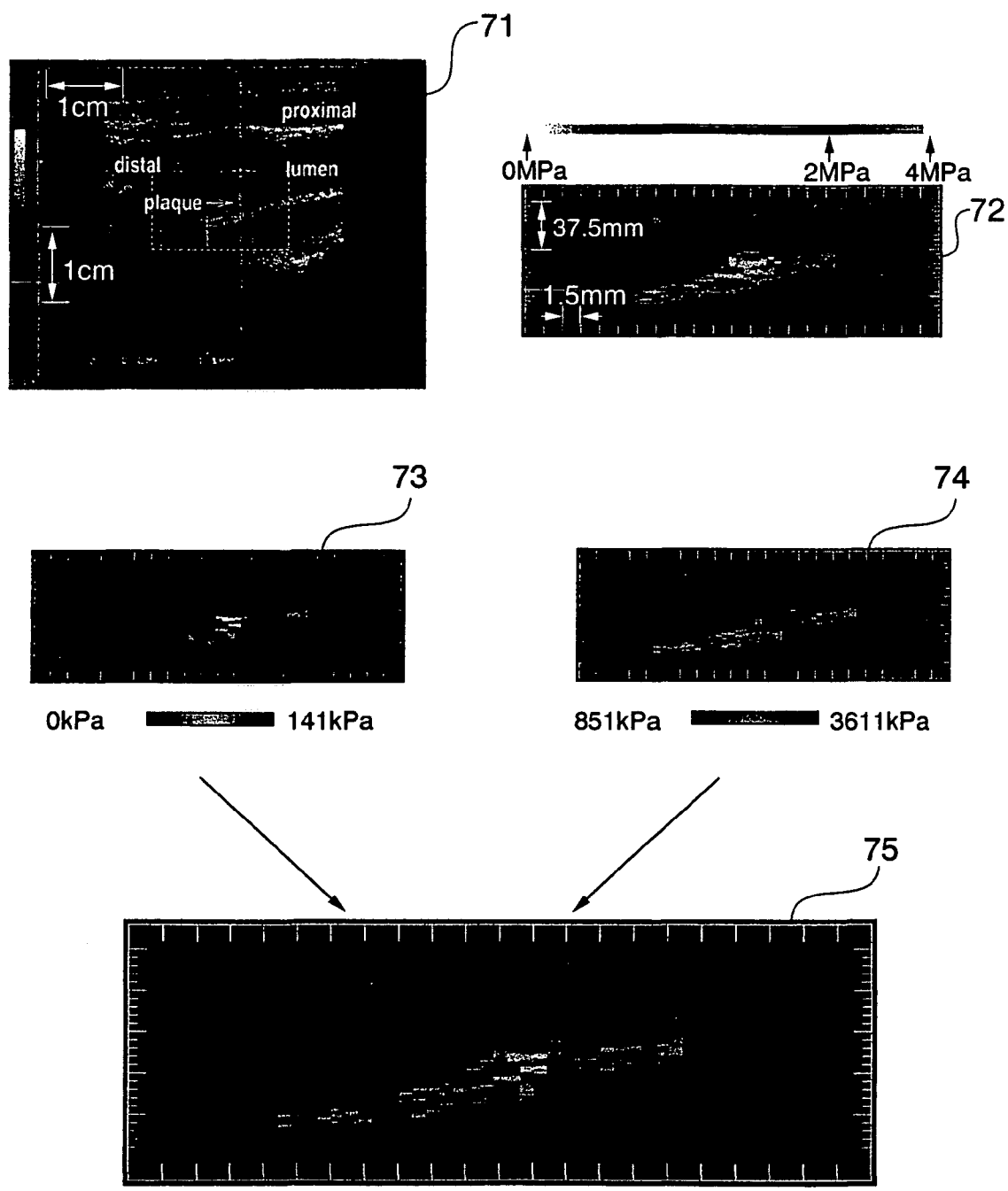
FIG. 7 is a diagram showing an example of tissue identification (52-year-old man).

Subsequently, FIGS. 5, 6, and 7 show the examples of actual measurements.

In FIG. 5, reference numerals 51 to 53 denote the examples of elasticity modulus measurement results of a fibrous tissue. An image 51 on the left shows an elasticity modulus tomogram and an image 52 shows the tomogram of a fibrous tissue. A graph 53 on the right shows the histogram of a fibrous tissue. In FIG. 5, reference numerals 54 to 56 denote the examples of elasticity modulus measurement results of a lipid-rich tissue. An image 54 on the left shows an elasticity modulus tomogram and an image 55 shows the tomogram of a lipid-rich tissue. A graph 56 on the right shows the histogram of a lipid-rich tissue.

FIGS. 6 and 7 show tissue discrimination examples of a 71-year-old man and a 52-year-old man. In FIGS. 6 and 7, reference numerals 61 and 71 denote B-mode images, reference numerals 62 and 72 denote elasticity modulus tomograms, reference numerals 63 and 73 denote the tomograms of a lipid-rich tissue, reference numerals 64 and 74 denote the tomograms of a fibrous tissue, and reference numerals 65 and 75 denote the electronic chromatic figures of a tissue.

Embodiment 2

In this example, the conventional problem is solved as follows: based on findings that tissues such as a lipid-rich area, a thrombus area, an elastic fiber, a collagen fiber, and a calcified area that are found on a blood vessel wall are different in viscosity in addition to hardness according to each tissue characteristic, the frequency distribution (histogram) of viscosity in addition to an elasticity value for each kind of tissue is acquired beforehand and is managed in a data library, each local elasticity value and viscosity value that are obtained in an ultrasonic diagnosis are compared with the frequency distribution of the elasticity values and viscosity values of the tissues in the data library, a tissue is discriminated by determining a tissue having a frequency distribution of the closest elasticity value and viscosity, and tissue type information is displayed, for example, in colors in a tomogram.

A motion such as the pulsation of a living tissue and a change in intravascular pressure have a low frequency band of 30 Hz or less. Thus, when a motion such as the pulsation of a living tissue and a change in intravascular pressure serve as external forces applied to a tissue, a measurement is considered to be static, though an amplitude is large. In the case of such a static measurement, it is necessary to measure a deformation of a tissue before and after a change in pressure and calculate an elasticity modulus by the calculation of (pressure change)/(distortion), (so called static technique). However, in reality, it is difficult to measure a pressure applied inside and a change in pressure in vivo.

Hence, the following method is proposed: a low-frequency sine wave oscillation (generally a single frequency component) is applied from the outside by using an oscillator and so on, the propagation velocity of a vibration (shear elasticity) is measured in vivo, and a parameter for a hardness of a tissue is calculated (external oscillation+dynamic method, Jpn J. Med Ultrasonics, Vol. 16, No. 3, pp. 221-229, 1989). In this method, it is not necessary to measure a pressure and a change in pressure. When a blood vessel wall is oscillated, although a bending oscillation can be readily excited so as to entirely bend a blood vessel wall, it is difficult to propagate a vibration so as to penetrate the wall from the outside to the inside of the blood vessel wall.

Hence, the present invention focuses attention on a fact that components such as a "turbulent flow" and a "vortex" that are generated by a time change in a pulse of a pulsatile flow in a blood vessel "excite vibrations of components over a wide frequency band of several tens Hz to several hundreds Hz on a blood vessel wall with a small amplitude of several mm/s or less." The wall vibration is accurately measured by using ultrasound and a waveform is analyzed, so that a propagation velocity and a propagation loss of a vibration (shear elastic wave) in vivo can be calculated at each frequency f.

Besides, (1) the vibrations excited by the "turbulent flow" and the "vortex" are small in amplitude (several mm/s or less) and (2) the position of the wall is moved by about several mm due to the arrival of pulsation. Thus, measurement could not be performed in vivo.

For example, in a conventional ultrasonic Doppler measurement technique, an average blood flow velocity of an area (several mm width) set in the lumen of a blood vessel is measured by frequency analysis on ultrasound reflected in a blood flow or correlation method. However, a target velocity in a blood flow measurement is several tens cm/s, which is larger than the vibration velocity of a blood vessel wall by two digits or more. Although the momentary magnitude of a blood flow velocity is considered important in a diagnosis, the waveform of the obtained blood flow velocity was not subjected to waveform analysis (frequency analysis) and so on.

In this example, an ultrasonic measurement method invented by the inventor (Japanese Patent Laid-Open No. 8-163418, U.S. Pat. No. 5,840,028) is adopted. With this method, a waveform with a small vibration velocity generated by pulsation on an arterial wall can be measured by using ultrasound. In the present invention, a waveform of wall vibration is measured by the ultrasonic measurement method simultaneously on a plurality of points set at intervals of several hundreds microns from the intima to the adventitia of a blood vessel wall on one ultrasonic beam.

Figure 8:
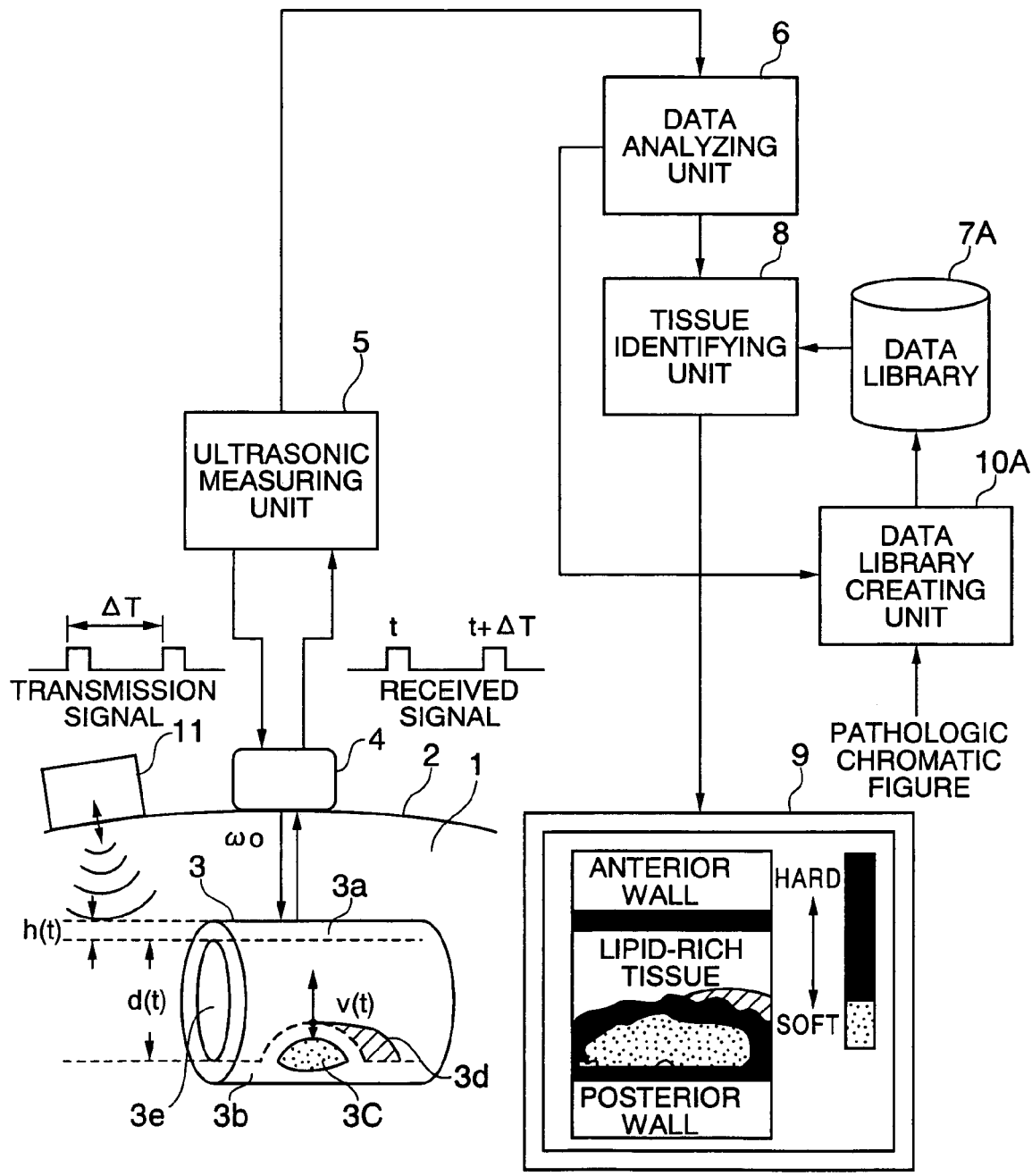
FIG. 8 is a schematic structural diagram showing another ultrasonic diagnostic system according to the present invention.

FIG. 8 shows a schematic structural diagram showing another ultrasonic diagnostic system according to the present invention.

FIG. 8 shows that the ultrasonic diagnostic system is further provided with a data library 7A instead of the elasticity data library 7, a data library creating unit 10A instead of the elasticity data library creating unit 10, and exciting means 11, in the structure of FIG. 1.

In addition to the elasticity data, the data library 7A stores viscosity data of living tissues that serves as previously inputted reference data, that is frequency distribution (histogram) data of a viscosity value for each kind of known living tissue.

In addition to the elasticity data, the data library creating unit 10A registers the frequency distribution of a viscosity for each kind of living tissue. That is, regarding data effectively acting as the reference data in viscosity tomogram data generated by a data analyzing unit 6, a comparison is made with a previously generated pathologic chromatic figure, so that the kind of living tissue is identified in each local area of the tomogram, and attribute data indicating the kind of living tissue is inputted and set in the viscosity tomogram data. Then, attribute data of each local area is examined, the distribution frequency of viscosities is obtained for each kind of living tissue, and the frequency distribution is registered in the data library 7A.

The embodiment of the ultrasonic diagnostic system of FIG. 8 will be described in detail. The following explanation will mainly discuss differences from Embodiment 1.

In accordance with the processing flow of FIG. 2E, for example, a waveform with a small vibration velocity v(t) that is generated on an arterial wall due to pulsation is measured (steps S11 to S13) by using the ultrasonic measurement method above-described (U.S. Pat. No. 5,840,028, which is incorporated by a reference in this specification). Thus, a waveform of wall vibration is measured simultaneously on a plurality of points set at intervals of several hundreds microns from the intima to the adventitia of a blood vessel wall on one ultrasonic beam. The amplitude is several mm/s or less and the frequency is a band of 0 Hz to several hundreds Hz.

Figure 9:
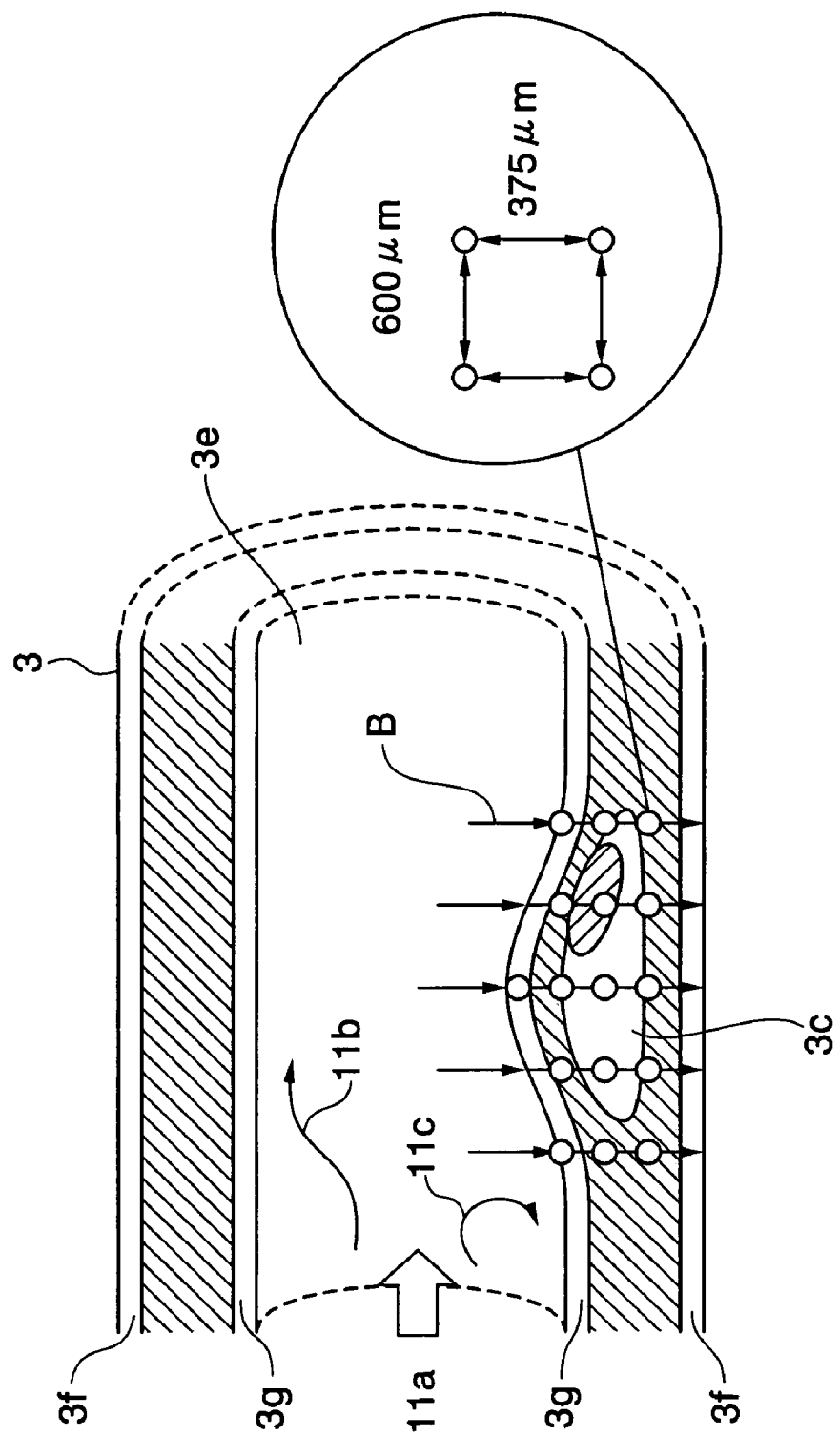
FIG. 9 is a conceptual drawing showing a vibration excited on a blood vessel wall.
Figure 11:
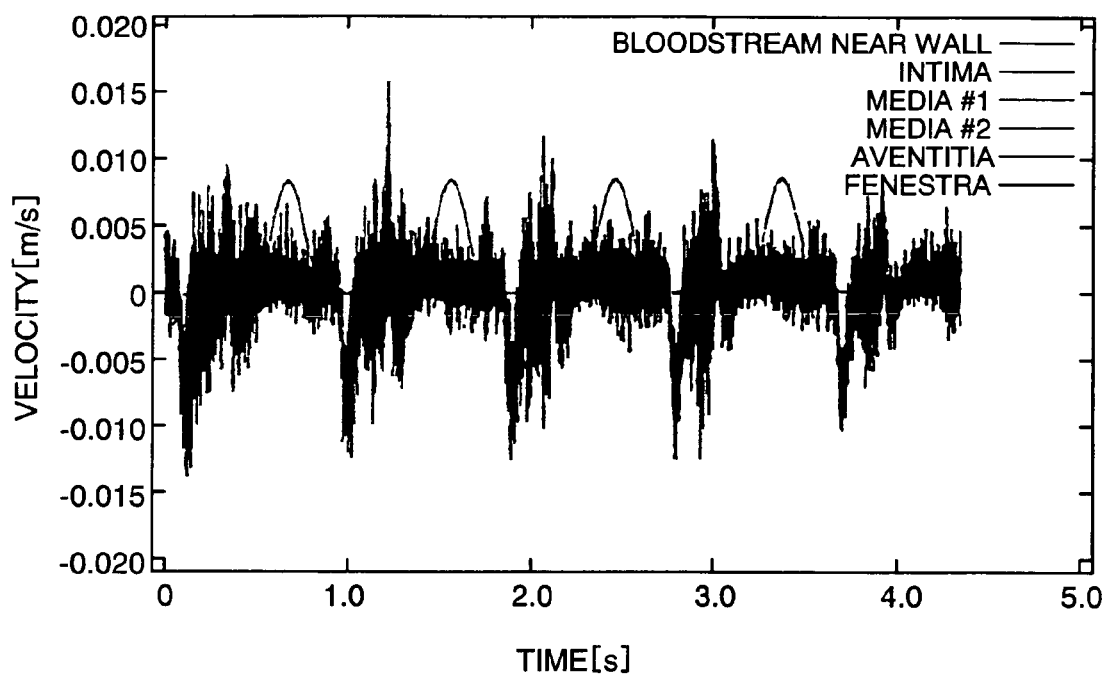
FIG. 11 is a diagram showing an example of a waveform of a small vibration velocity v(t) on a blood vessel wall.

At the measurement, as shown in FIG. 9, a pulse wave 11a caused by pulsation propagates through a lumen 3e of a blood vessel 3 and a lesion 3c causes a turbulent flow 11b or a vortex 11c. The turbulent flow 11b and the vortex 11c, each serving as a vibration source, vibrate the wall of the blood vessel 3 in the above-described manner. Thus, a vibration v(t) is measured on each point (white circle) by an ultrasonic beam B. Reference numeral 3f denotes the adventitia of the blood vessel wall. Reference numeral 3g denotes the intima of the blood vessel wall. The measured vibration v(t) is shown in FIG. 11. FIG. 11 shows measurement results in a period of four pulses. It is found that each point vibrates according to pulsation.

A pulse wave 11a may be generated by pulsation. That is, any structure is applicable as long as an inner product is changed by excited bending oscillation (of blood vessel 3) and thus an internal pressure change ΔP(f) is excited as shown in FIG. 10B. Reference character "f" denotes a frequency at which a vibration source vibrates. The inner pressure change ΔP(f) propagates as the pulse wave 11a. Therefore, for example, a vibration on a measured part 3h (FIG. 10) is excited by the component of the turbulent flow 11b or the vortex 11c which are generated by a time change in a pulse of a pulsatile flow in the blood vessel 3.

Further, as shown in FIG. 10A, the pulse wave 11a may be generated by the exciting means 11. The vertical vibration of the exciting means 11 at the frequency "f" excites the internal pressure change ΔP(f). Therefore, for example, the vibration on the measured part 3h is excited by a vibration percutaneously applied to a part away from the measured part 3h from the outside of the body.

Figure 12:
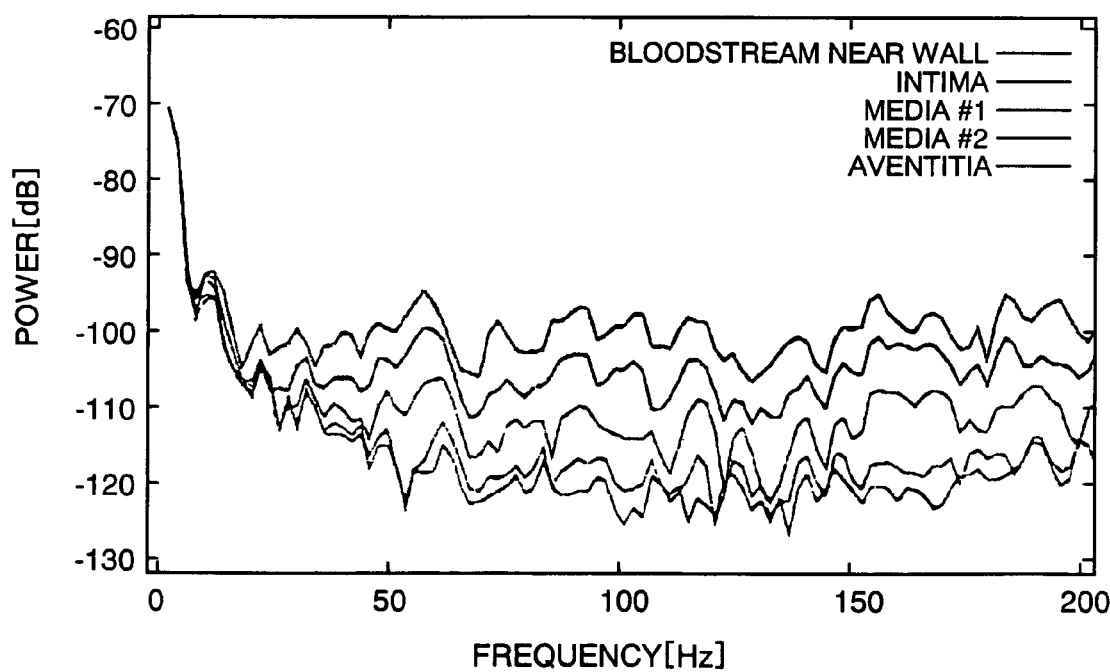
FIG. 12 is a diagram showing a power spectrum obtained by frequency analysis.

Moreover, instead of steps S14 to S16 of FIG. 2E, waveforms are cut out at the same timing in a pulse and frequency analysis is performed (while a window is applied in a diastole), so that a transfer function H(f) from a vibration waveform vm(t) at m point on the intima to a vibration waveform vn(t) at n-th point of the adventitia is calculated. That is, the power spectrum of FIG. 12 is obtained by the frequency analysis. When a distance is d between the two points in the power spectrum, an attenuation constant $\alpha(f)=|H(f)|/d$ associated with propagation between the two points can be calculated from an amplitude $|H(f)|$. Moreover, a phase velocity $v(f)=2\pi f/(\angle H(f)/d)$ of propagation between the two points can be calculated from a phase $\angle H(f)$ of the transfer function.

Figure 13A:
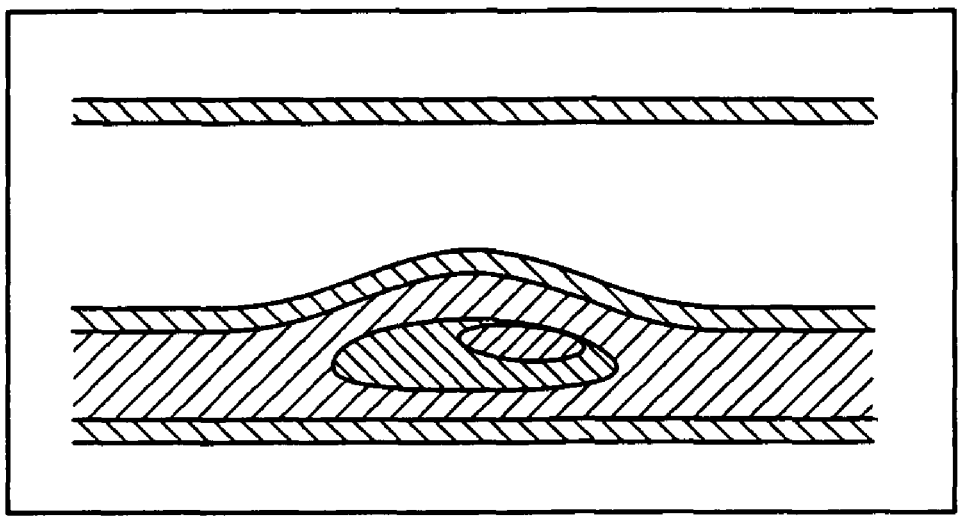
FIG. 13A shows a tomogram of attenuation.
Figure 13B:
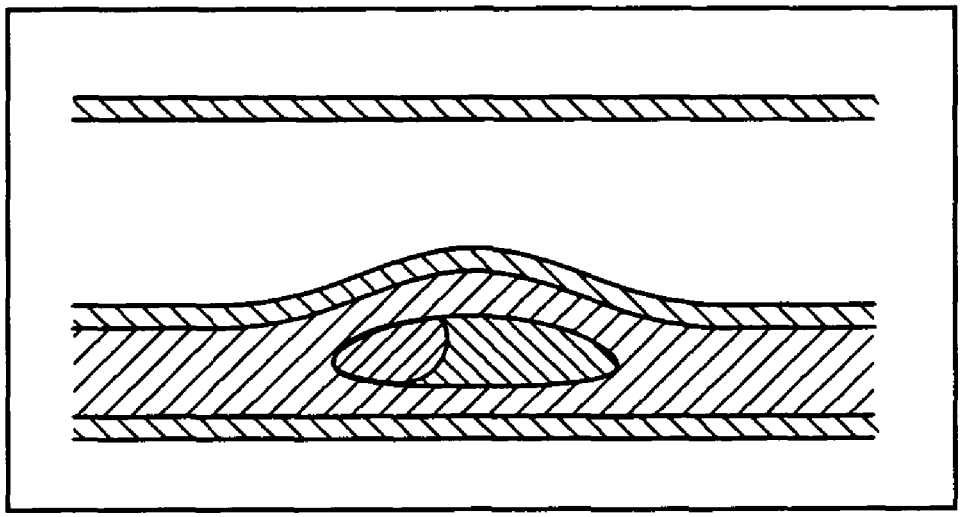
FIG. 13B shows a tomogram of a phase velocity.

A tomogram on the attenuation of FIG. 13A can be obtained from the attenuation constant α(f). Further, a tomogram of the phase velocity of FIG. 13B can be obtained from the phase velocity v(f). Comparison between the tomograms proves that the single lesion 3c includes both of a lesion shown in the tomogram of attenuation and a lesion show in the tomogram of phase velocity.

Based on the two parameters, a complex propagation constant $\gamma(f)=\alpha(f)+j\beta(f)$ is determined where "j" represents an imaginary unit and $\beta(f)=\omega/v(f)$ and $\omega=2\pi f$ are established. γ(f) indicates that a propagation per unit length has an attenuation of α(f) and a phase rotation of β(f).

According to a document (J. Biomechanics, vol. 28, No. 10, pp. 1145 to 1154, 1995), the complex propagation constant γ(f) has the relationship of $$\mu+j\omega\eta=-\rho\omega^2/\gamma^2(f)$$

between a shear (or shearing) elastic constant (a modulus of rigidity) μ and a shear viscosity constant η. When a measured complex transfer constant γ(f) is substituted into the right side of the formula and a real item and an imaginary item are arranged, the shear elastic constant μ and the shear viscosity constant η are expressed by the formulas below.

$$\mu=-\rho\omega^2(\alpha^2(f)-\beta^2(f))/\Delta$$

$$\eta=2\rho\omega\alpha(f)\beta(f)/\Delta$$

Where, $$\Delta=(\alpha^2(f)-\beta^2(f))^2+(2\alpha(f)\cdot\beta(f))^2$$

is established. Thus, a shear elastic constant μ and a shear viscosity constant η are calculated for a small area between the point m and the point n on one ultrasonic beam (step S16).

The above-described measurement is performed on each point of the lesion in and on the arterial wall on one ultrasonic beam (step S17). The point is set with the order of a waveform of a used ultrasonic wave, for example, at intervals of 375 microns. Further, an ultrasonic beam is scanned in real time along the axial direction of the blood vessel wall at intervals of 150 microns (FIG. 9). Thus, a tomogram with the shear elastic constant μ and the shear viscosity constant η is extracted in each local area of 375 microns×150 microns (step S18).

Figure 14A:
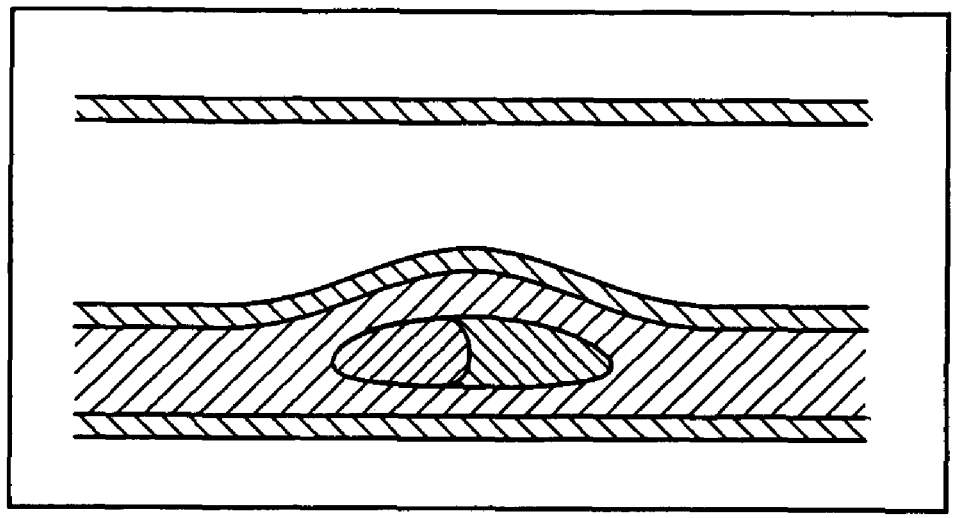
FIG. 14A shows a tomogram of a shear elasticity modulus.
Figure 14B:
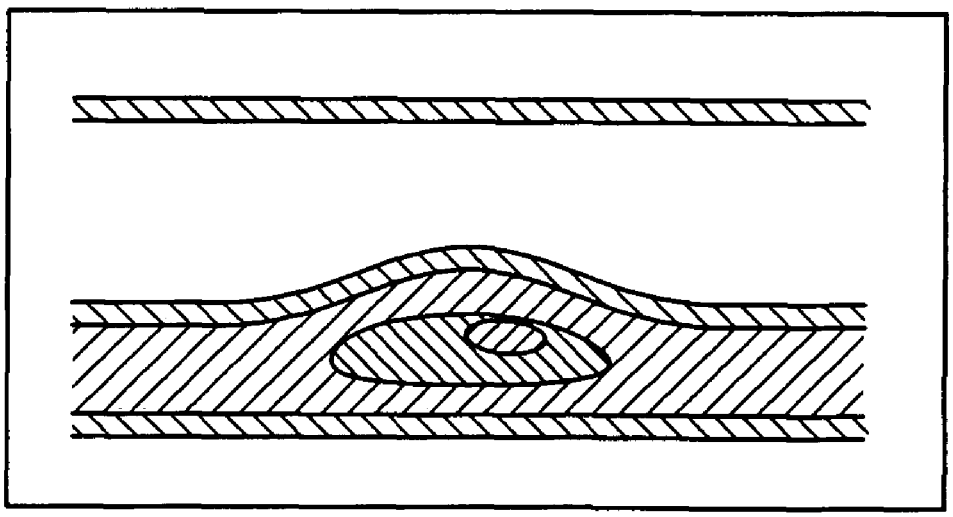
FIG. 14B shows a tomogram of a shear viscosity.

A tomogram of a shear elasticity modulus shown in FIG. 14A can be obtained from the shear elastic constant (i.e., shear elasticity modulus) μ. Moreover, a tomogram of a shear viscosity shown in FIG. 14B can be obtained from the shear viscosity constant (i.e., shear viscosity) η. The tomogram of the shear elasticity modulus shown in FIG. 14A corresponds to the tomogram of a phase velocity shown in FIG. 13B, and the tomogram of the shear viscosity shown in FIG. 14B corresponds to the tomogram of attenuation shown in FIG. 13A.

Figure 15:
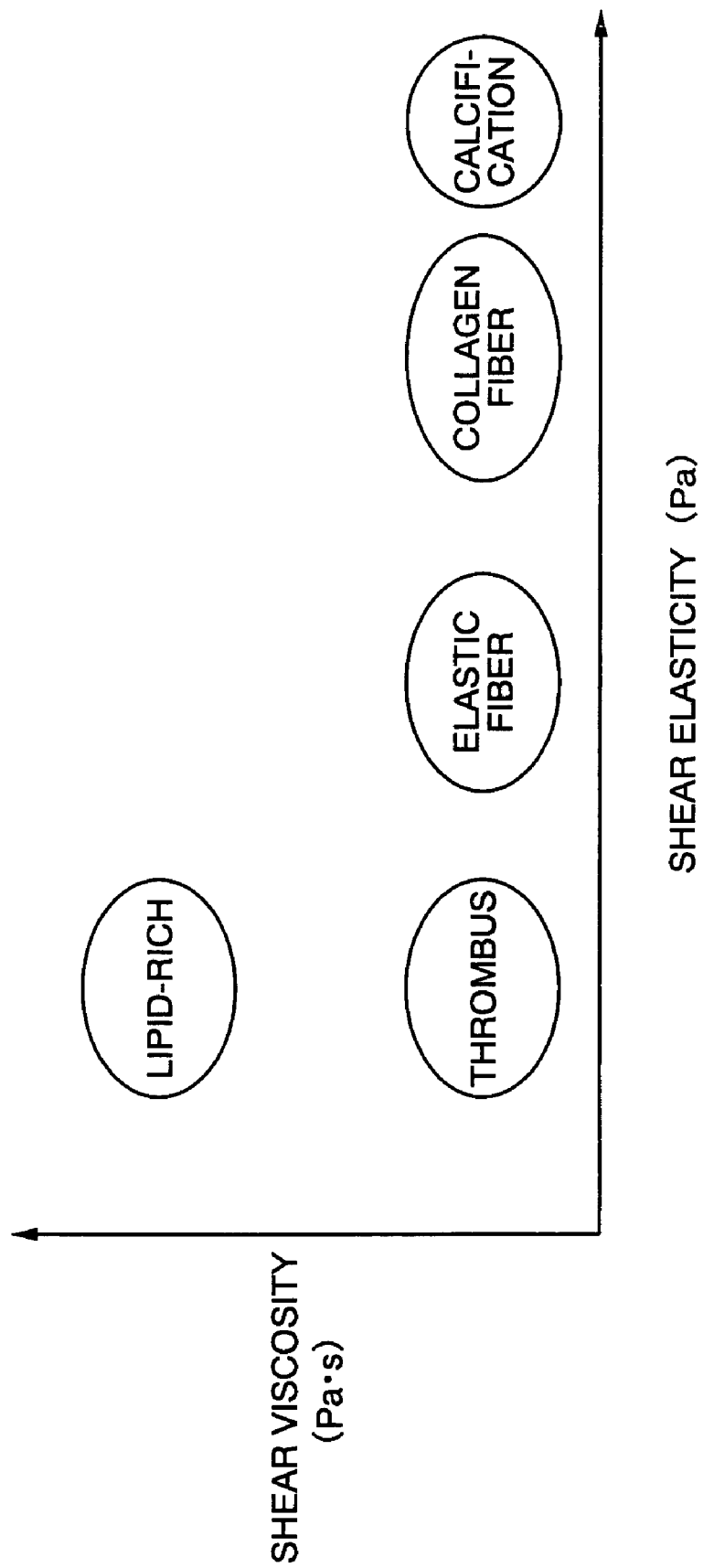
FIG. 15 is a diagram showing an example of the data library where tissues are mapped on a two-dimensional plane.

As with the processing of FIG. 3, regarding a representative lesion, the shear elastic constant μ and the shear viscosity constant η that are obtained on each point are compared with a pathologic chromatic figure and data of elasticity and viscosity of tissues such as lipid-rich, thrombus, elastic fiber, collagen fiber and calcification is registered in the data library 7A. At this point of time, as shown in FIG. 15, the tissues are mapped on a two-dimensional plane where the vertical axis represents a shear viscosity (Pa·s) and the horizontal axis represents a shear elasticity modulus (Pa), so that registration is performed. In this way, classification can be performed on the two-dimensional plane by using an elastic characteristic and a viscous characteristic, thereby increasing the accuracy of the data library 7A. For example, it is possible to identify a thrombus area, an elastic fiber, a collagen fiber, and a calcified area that are hard to identify only based on a shear viscosity. Further, it is possible to identify a lipid-rich area and a thrombus area that are hard to identify only based on a shear elasticity modulus.

Figure 16:
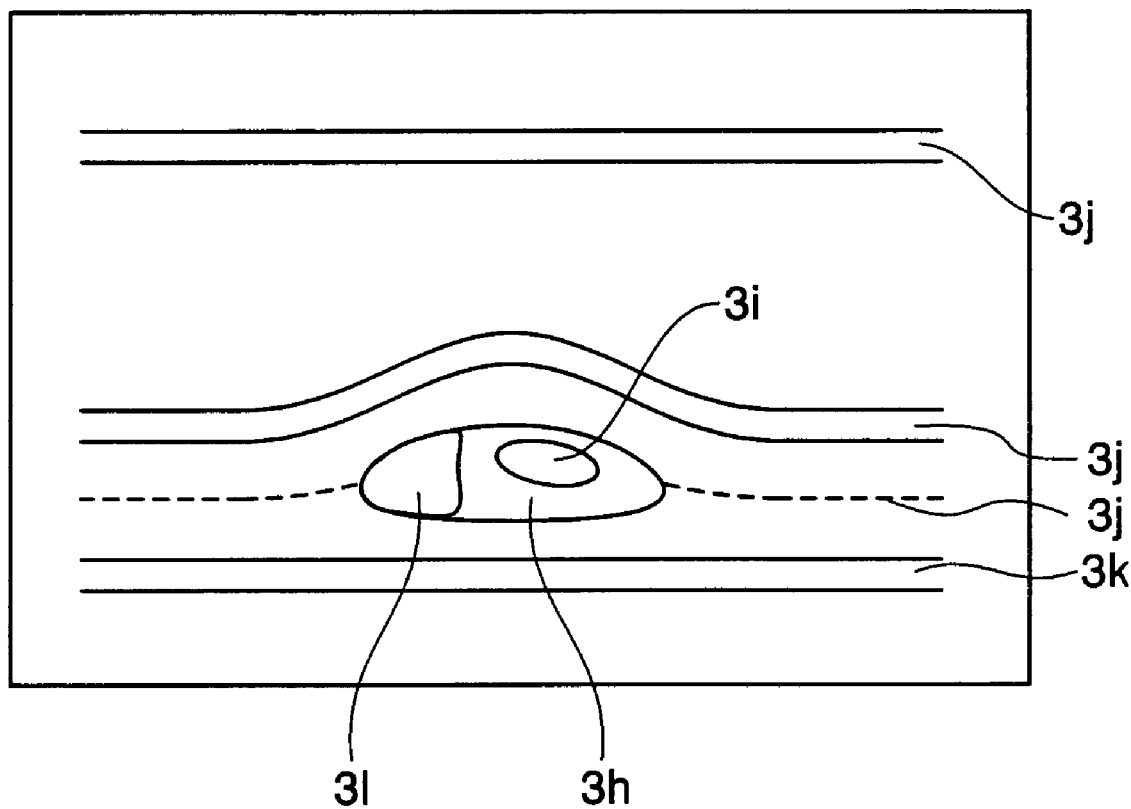
FIG. 16 is a conceptual drawing showing an example of a tomogram having undergone electronic dyeing.
Figure 17:
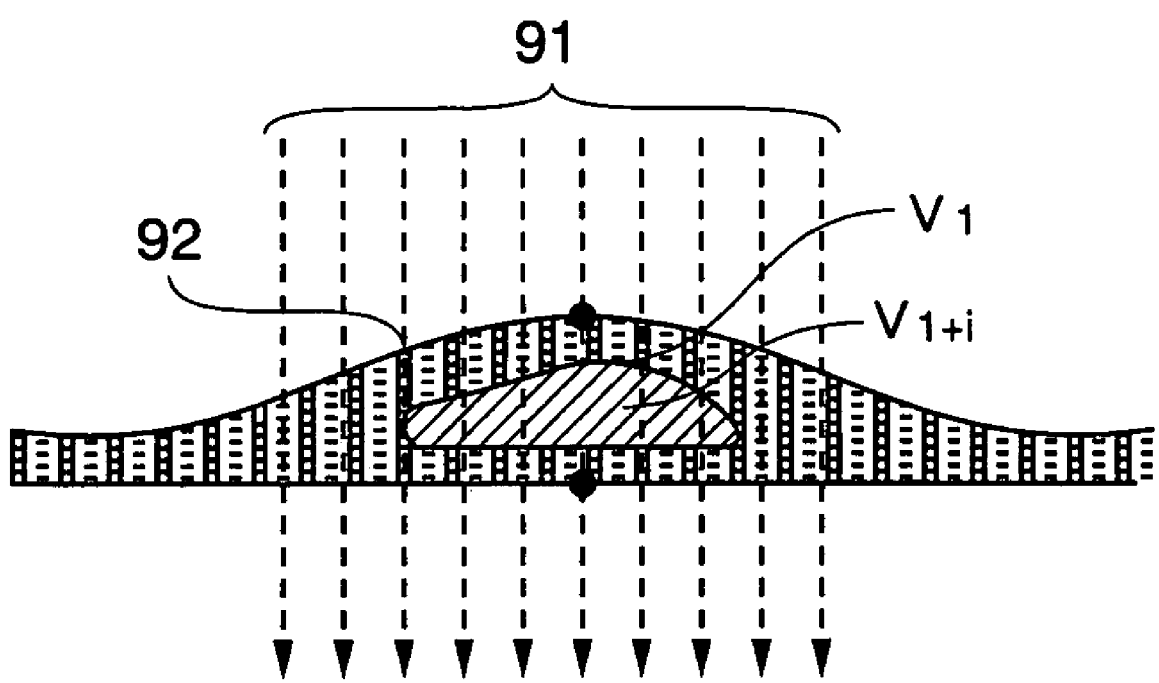
FIG. 17 is a diagram showing an image of elasticity modulus distribution of an atheroma on a carotid wall.

Then, as with the processing of FIG. 4, on the tomogram of the shear elastic constant μ and shear viscosity constant η to be actually measured, a tissue characteristic is identified on each local area with reference to the data library 7A and electronic dyeing is performed. Thus, as shown in FIG. 16, tissues such as a lipid-rich area 3h, a thrombus area 3i, an elastic fiber 3*j*, a collagen fiber 3*k*, and a calcified area 3*l* can be clearly displayed on a screen by electronic dyeing.

Besides, as with the elasticity data of Embodiment 1, the kind of living tissue to be diagnosed may be identified only based on viscosity data acquired in the above-described manner.

INDUSTRIAL APPLICABILITY

According to the present invention, in an ultrasonic diagnosis of a living tissue such as a lesion in a blood vessel, it is possible to readily identify the kind of living tissue such as a lipid-rich area, a thrombus area, an elastic fiber, a collagen fiber, and a calcified area on an ultrasonic diagnostic image. Thus, a noninvasive diagnosis can be performed in a clinical diagnosis more properly and quickly as compared with the conventional art.

For example, the present invention makes it possible to predict the rupture of an atheroma (arteriosclerotic plaque) that is a main cause of an acute cardiovascular event such as unstable angina, acute myocardial infarction, and sudden death. Such a prediction is impossible in a noninvasive manner in the conventional art.

It is considered that a serious cardiovascular disease such as myocardial infarction and cerebral infarction is caused by the clogging of a thrombus in the lumen of a blood vessel, the thrombus being formed by the rupture of an arteriosclerotic plaque (atheroma), which is formed on an arterial wall and is rich in lipid-rich. The present invention can evaluate the stability of an atherosclerotic lesion in a noninvasive manner.

Further, the present invention can evaluate the curative effect of a cholesterol lowering treatment.

What is claimed is:

1. A method for identifying a living tissue in an ultrasonic diagnosis, the method comprising the steps of:
    measuring displacement on a local area of a living tissue to be diagnosed in a single pulse of a pulsatile flow from a heart via ultrasound to track a large amplitude motion of said local area in said single pulse of said pulsatile flow, said local area being a part of a wall of an artery, said displacement being excited by a turbulent flow component and a vortex component in the artery, said turbulent flow component and said vortex component being generated by said pulsatile flow in the artery;
    calculating a maximum value of a thickness change of said wall of the artery in said single pulse of said pulsatile flow based on said tracked large amplitude motion of said local area in said single pulse of said pulsatile flow;
    calculating a shear elasticity or a shear viscosity of said local area based on said calculated maximum value of said thickness change of said wall of said local area;
    preparing, in a data library, elasticity data or viscosity data for a plurality of types of living tissue, said types of living tissue including an adipose area, a thrombus area, an elastic fiber, a collagen fiber, and a calcified area, said elasticity data including an elasticity modulus frequency histogram associated with each of the plurality of types of living tissue, said viscosity data including a viscosity modulus frequency histogram associated with each of the plurality of types of living tissue; and
    identifying one or more types of living tissue of said local area by comparing said measured shear elasticity with said elasticity data or said measured shear viscosity with said viscosity data.

2. The method for identifying a living tissue in an ultrasonic diagnosis according to claim 1, wherein in preparing the data library, each type of living tissue is mapped on a two-dimensional plane having axes representing a shear elasticity modulus and a shear viscosity.

3. An ultrasonic diagnostic system, in which at least an elasticity of a living tissue to be diagnosed is measured in an area by using ultrasound and a tomogram is displayed, the system comprising:
    an ultrasound means for measuring displacement on a local area of a living tissue in a single pulse of a pulsatile flow from a heart to track a large amplitude motion of said local area in said single pulse of said pulsatile flow, said local area comprising a portion of a wall of an artery, said pulsatile flow generating a turbulent flow and a vortex in the artery, said displacement being produced via said turbulent flow and said vortex;
    a means for calculating a maximum value of a thickness change of said wall of the artery in said single pulse of said pulsatile flow based on said tracked large amplitude motion of said local area in said single pulse of said pulsatile flow and for determining a shear elasticity or a shear viscosity of said local area based on said calculated maximum value of said thickness change of said wall of said local area;
    a data library for compiling elasticity data or viscosity data for a plurality of types of living tissue including an adipose area, a thrombus area, an elastic fiber, a collagen fiber, and a calcified area, said elasticity data including an elasticity modulus frequency histogram associated with each of said plurality of types of living tissue of said data library, said viscosity data including a viscosity modulus frequency histogram associated with each of said plurality of types of living tissue of said data library to provide a compilation of said elasticity data or said viscosity data; and
    a tissue identifying unit receiving said measured shear elasticity or said measured shear viscosity, said tissue identifying unit comparing said measured shear elasticity or said measured shear viscosity with said elasticity data or said viscosity data to identify one or more types of living tissue of said local area.

4. The ultrasonic diagnostic system according to claim 3, wherein each type of living tissue is mapped on a two-dimensional plane having axes representing a shear elasticity modulus and a shear viscosity.

5. The ultrasonic diagnostic system according to claim 3, wherein the living tissue to be diagnosed is a living tissue on a blood vessel.

6. The ultrasonic diagnostic system according to claim 3, wherein the tissue identifying unit has identifying means which refers to the elasticity data for each type of living tissue, the data being extracted from the data library, and determines the type of living tissue having a minimum distance, for each elasticity data serving as a measurement result in each local small area.

7. The ultrasonic diagnostic system according to claim 6, wherein the identifying means determines dispersion and an average value of elasticity moduli from the histogram of elasticity data of each type of living tissue, the data being extracted from the data library, and the identifying means performs identification using Bayes decision method.

8. A method for identifying a living tissue in an ultrasonic diagnosis, the method comprising the steps of:
    measuring displacement of a local area of the living tissue in a single pulse of a pulsatile flow from a heart with an ultrasonic wave such that a large amplitude motion of said local area in said single pulse of said pulsatile flow is tracked, said local area being a portion of a wall of an artery, said pulsatile flow generating a turbulent flow and a vortex in the artery, said displacement of said local area being produced via said turbulent flow and said vortex;

determining a maximum value of a thickness change of said wall of the artery in said single pulse of said pulsatile flow based on said tracked large amplitude motion of said local area in said single pulse of said pulsatile flow;

determining a shear elasticity or a shear viscosity of said local area based on said determined maximum value of said thickness change of said wall of said local area;

compiling elasticity data or viscosity data for a plurality of types of living tissue including an adipose area, a thrombus area, an elastic fiber, a collagen fiber and a calcified area, said elasticity data comprising an elasticity modulus frequency distribution associated with each of said plurality of types of living tissue, said viscosity data comprising a viscosity modulus frequency distribution associated with each of said plurality of types of living tissue;

storing said elasticity data or said viscosity data in a data library;

comparing said measured shear elasticity or said measured shear viscosity with said elasticity modulus frequency distribution of said elasticity data or said viscosity frequency distribution;

determining one or more types of living tissue of said local area based on said comparison of said measured shear elasticity or said measured shear viscosity with said elasticity data or said viscosity data.

9. The method for identifying a living tissue in an ultrasonic diagnosis according to claim 8, further comprising the step of displaying tissue information as a tomogram based on said comparison of said shear elasticity with said elasticity data.

* * * * *